(12) United States Patent
Lukacs et al.

(10) Patent No.: US 8,316,518 B2
(45) Date of Patent: Nov. 27, 2012

(54) METHODS FOR MANUFACTURING ULTRASOUND TRANSDUCERS AND OTHER COMPONENTS

(75) Inventors: Marc Lukacs, Toronto (CA); Chris Chaggares, Oshawa (CA); Desmond Hirson, Thornhill (CA); Guofeng Pang, Ajax (CA)

(73) Assignee: VisualSonics Inc., Toronto (CA)

( * ) Notice: Subject to any disclaimer, the term of this patent is extended or adjusted under 35 U.S.C. 154(b) by 47 days.

(21) Appl. No.: 12/562,998

(22) Filed: Sep. 18, 2009

(65) Prior Publication Data

US 2010/0156244 A1 Jun. 24, 2010

Related U.S. Application Data

(60) Provisional application No. 61/192,661, filed on Sep. 18, 2008, provisional application No. 61/192,690, filed on Sep. 18, 2008.

(51) Int. Cl.
*H04R 17/10* (2006.01)
*B23K 26/38* (2006.01)
*H05K 3/08* (2006.01)

(52) U.S. Cl. ............ 29/25.35; 29/594; 29/854; 29/847; 219/121.67; 219/121.69; 219/121.85

(58) Field of Classification Search ................. 29/25.35, 29/594, 846, 847, 832, 854; 219/121.67, 219/121.68, 121.69, 121.85; 310/334, 363
See application file for complete search history.

(56) References Cited

U.S. PATENT DOCUMENTS

| 2,205,169 | A |   | 5/1937  | Hallman         |
|-----------|---|---|---------|-----------------|
| 3,922,572 | A |   | 11/1975 | Cook et al.     |
| 4,217,684 | A |   | 8/1980  | Brisken et al.  |
| 4,360,007 | A |   | 11/1982 | Levy et al.     |
| 4,385,255 | A |   | 5/1983  | Yamaguchi et al.|
| 4,543,829 | A |   | 10/1985 | Lerch           |
| 4,617,707 | A |   | 10/1986 | Mohaupt et al.  |
| 4,684,436 | A | * | 8/1987  | Burns et al. .......... 219/121.85 X |
| 4,802,099 | A |   | 1/1989  | Logue           |
| 4,809,184 | A |   | 2/1989  | O'Donnell et al.|
| 4,841,977 | A |   | 6/1989  | Griffith et al. |
| 4,945,155 | A |   | 7/1990  | Fagerburg et al.|
| 5,014,710 | A |   | 5/1991  | Maslak et al.   |
| 5,045,746 | A |   | 9/1991  | Wersing et al.  |
| 5,123,415 | A |   | 6/1992  | Daigle          |
| 5,160,870 | A |   | 11/1992 | Carson et al.   |
| 5,186,177 | A |   | 2/1993  | O'Donnell et al.|
| 5,203,335 | A |   | 4/1993  | Noujaim et al.  |

(Continued)

FOREIGN PATENT DOCUMENTS

DE 41 42 372 6/1993

(Continued)

OTHER PUBLICATIONS

Bridal et al., "Milestones on the Road to Higher Resolution, Quantitative, and Functional Ultrasonic Imaging," *Proceedings of the IEEE* 91:1543-1561, 2003.

(Continued)

*Primary Examiner* — A. Dexter Tugbang

(57) ABSTRACT

Methods for the manufacture of electrical components, such as ultrasound transducers, are illustrated and described. In particular, several embodiments of the methods can include patterning electrodes, such as for the connection of an ultrasound transducer to an electrical circuit. The methods also can include depositing metal on surfaces and making an integrated matching layer for an ultrasound transducer. Ultrasound transducers produced by these methods also are illustrated and described.

40 Claims, 12 Drawing Sheets

U.S. PATENT DOCUMENTS

| | | | |
|---|---|---|---|
| 5,311,095 A | 5/1994 | Smith et al. |
| 5,318,033 A | 6/1994 | Savord |
| 5,325,860 A | 7/1994 | Seward et al. |
| 5,329,496 A | 7/1994 | Smith |
| 5,345,426 A | 9/1994 | Lipschutz et al. |
| 5,345,940 A | 9/1994 | Seward et al. |
| 5,360,007 A | 11/1994 | Shinomura et al. |
| 5,368,037 A | 11/1994 | Eberle et al. |
| 5,369,624 A | 11/1994 | Fukukita et al. |
| 5,371,717 A | 12/1994 | Bolorforosh |
| 5,388,079 A | 2/1995 | Kim et al. |
| 5,390,674 A | 2/1995 | Robinson et al. |
| 5,392,259 A | 2/1995 | Bolorforosh |
| 5,406,163 A | 4/1995 | Carson et al. |
| 5,410,516 A | 4/1995 | Uhlendorf et al. |
| 5,415,175 A | 5/1995 | Hanafy et al. |
| 5,434,827 A | 7/1995 | Bolorforosh |
| RE35,011 E | 8/1995 | Wersing et al. |
| 5,438,554 A | 8/1995 | Seyed-Bolorforosh et al. |
| 5,438,998 A | 8/1995 | Hanafy |
| 5,445,155 A | 8/1995 | Sieben |
| 5,453,575 A | 9/1995 | O'Donnell et al. |
| 5,456,259 A | 10/1995 | Barlow et al. |
| 5,460,181 A | 10/1995 | Seyed-Bolorforosh |
| 5,465,725 A | 11/1995 | Seyed-Bolorforosh |
| 5,505,088 A | 4/1996 | Chandraratna et al. |
| 5,522,391 A | 6/1996 | Beaudin et al. |
| 5,544,655 A | 8/1996 | Daigle |
| 5,548,564 A | 8/1996 | Smith |
| 5,553,035 A | 9/1996 | Seyed-Bolorforosh et al. |
| 5,573,001 A | 11/1996 | Petrofsky et al. |
| 5,577,506 A | 11/1996 | Dias |
| 5,582,177 A | 12/1996 | Hanafy et al. |
| 5,603,327 A | 2/1997 | Eberle et al. |
| 5,629,865 A | 5/1997 | Roth |
| 5,653,236 A | 8/1997 | Miller |
| 5,655,276 A | 8/1997 | Pattanayak et al. |
| 5,667,373 A | 9/1997 | Wright et al. |
| 5,704,105 A | 1/1998 | Venkataramani et al. |
| 5,704,361 A | 1/1998 | Seward et al. |
| 5,706,819 A | 1/1998 | Hwang et al. |
| 5,713,363 A | 2/1998 | Seward et al. |
| 5,743,855 A | 4/1998 | Hanafy et al. |
| 5,744,898 A | 4/1998 | Smith et al. |
| 5,779,644 A | 7/1998 | Eberle et al. |
| 5,792,058 A | 8/1998 | Lee et al. |
| 5,795,297 A | 8/1998 | Daigle |
| 5,797,847 A | 8/1998 | Miller et al. |
| 5,834,880 A | 11/1998 | Venkataramani et al. |
| 5,844,139 A | 12/1998 | Miller et al. |
| 5,855,049 A * | 1/1999 | Corbett et al. ............... 29/25.35 |
| 5,857,974 A | 1/1999 | Eberle et al. |
| 5,865,749 A | 2/1999 | Doten et al. |
| 5,879,303 A | 3/1999 | Averkiou et al. |
| 5,895,855 A | 4/1999 | Ishikawa et al. |
| 5,897,501 A | 4/1999 | Wildes et al. |
| 5,905,692 A | 5/1999 | Dolazza et al. |
| 5,906,580 A | 5/1999 | Kline-Schoder et al. |
| 5,938,612 A | 8/1999 | Kline-Schoder et al. |
| 5,938,615 A | 8/1999 | Eberle et al. |
| 5,940,123 A | 8/1999 | Daigle et al. |
| 5,970,025 A | 10/1999 | Cole et al. |
| 5,976,090 A | 11/1999 | Hanafy et al. |
| 5,977,691 A | 11/1999 | Stephens et al. |
| 6,001,062 A | 12/1999 | Masters |
| 6,029,116 A | 2/2000 | Wright et al. |
| 6,034,922 A | 3/2000 | Uhlendorf et al. |
| 6,039,693 A | 3/2000 | Seward et al. |
| 6,049,958 A | 4/2000 | Eberle et al. |
| 6,050,945 A | 4/2000 | Peterson et al. |
| 6,063,034 A | 5/2000 | Doten et al. |
| 6,064,628 A | 5/2000 | Uhlendorf et al. |
| 6,073,045 A | 6/2000 | Dyson et al. |
| 6,083,164 A | 7/2000 | Oppelt et al. |
| 6,099,475 A | 8/2000 | Seward et al. |
| 6,110,116 A | 8/2000 | Wright et al. |
| 6,123,673 A | 9/2000 | Eberle et al. |
| 6,128,958 A | 10/2000 | Cain |
| 6,129,672 A | 10/2000 | Seward et al. |
| 6,129,677 A | 10/2000 | Sohma et al. |
| 6,135,971 A | 10/2000 | Hutchinson et al. |
| 6,183,578 B1 | 2/2001 | Ritter et al. |
| 6,193,662 B1 | 2/2001 | Hwang |
| 6,221,017 B1 | 4/2001 | Uhlendorf et al. |
| 6,235,024 B1 | 5/2001 | Tu |
| 6,236,144 B1 | 5/2001 | Millar et al. |
| 6,238,481 B1 | 5/2001 | Yamashita et al. |
| 6,251,073 B1 | 6/2001 | Imran et al. |
| 6,262,749 B1 | 7/2001 | Finger et al. |
| 6,278,224 B1 | 8/2001 | Sawada et al. |
| 6,283,920 B1 | 9/2001 | Eberle et al. |
| 6,306,096 B1 | 10/2001 | Seward et al. |
| 6,315,725 B1 | 11/2001 | Masters |
| 6,322,505 B1 | 11/2001 | Hossack et al. |
| 6,350,238 B1 | 2/2002 | Olstad et al. |
| 6,363,033 B1 | 3/2002 | Cole et al. |
| 6,403,396 B1 | 6/2002 | Gudesen et al. |
| 6,417,857 B2 | 7/2002 | Finger et al. |
| 6,437,487 B1 | 8/2002 | Mohr, III et al. |
| 6,443,899 B2 | 9/2002 | Uhlendorf et al. |
| 6,457,365 B1 | 10/2002 | Stephens et al. |
| 6,492,762 B1 | 12/2002 | Pant et al. |
| 6,497,664 B1 | 12/2002 | Randall et al. |
| 6,530,887 B1 | 3/2003 | Gilbert et al. |
| 6,544,180 B1 | 4/2003 | Doten et al. |
| 6,547,731 B1 | 4/2003 | Coleman et al. |
| 6,558,323 B2 | 5/2003 | Wakabayashi et al. |
| 6,558,326 B2 | 5/2003 | Pelissier |
| 6,608,371 B2 | 8/2003 | Kurashima et al. |
| 6,612,989 B1 | 9/2003 | Brock-Fisher |
| 6,618,916 B1 | 9/2003 | Eberle et al. |
| 6,626,838 B2 | 9/2003 | Doten et al. |
| 6,635,019 B2 | 10/2003 | Davidsen |
| 6,641,540 B2 | 11/2003 | Fleischman et al. |
| 6,650,264 B1 | 11/2003 | Chan et al. |
| 6,656,124 B2 | 12/2003 | Flesch et al. |
| 6,664,717 B1 | 12/2003 | Mohr, III et al. |
| 6,673,018 B2 | 1/2004 | Friedman |
| 6,676,606 B2 | 1/2004 | Simpson et al. |
| 6,679,845 B2 | 1/2004 | Ritter et al. |
| 6,685,644 B2 | 2/2004 | Seo et al. |
| 6,685,657 B2 | 2/2004 | Jones |
| 6,695,783 B2 | 2/2004 | Henderson et al. |
| 6,705,992 B2 | 3/2004 | Gatzke |
| 6,740,037 B1 | 5/2004 | Schoenfeld |
| 6,759,791 B2 | 7/2004 | Hatangadi et al. |
| 6,761,688 B1 | 7/2004 | Mohr, III et al. |
| 6,761,697 B2 | 7/2004 | Rubinstenn et al. |
| 6,780,157 B2 | 8/2004 | Stephens et al. |
| 6,784,600 B2 | 8/2004 | Klee et al. |
| 6,787,974 B2 | 9/2004 | Fjield et al. |
| 6,806,623 B2 | 10/2004 | Petersen et al. |
| 6,821,253 B2 | 11/2004 | Wakabayashi et al. |
| 6,822,189 B2 | 11/2004 | Hong et al. |
| 6,822,374 B1 | 11/2004 | Smith et al. |
| 6,822,376 B2 | 11/2004 | Baumgartner |
| 6,837,855 B1 | 1/2005 | Puech |
| 6,851,392 B2 | 2/2005 | Zan et al. |
| 6,873,090 B2 | 3/2005 | Shiraishi et al. |
| 6,875,178 B2 | 4/2005 | Phelps et al. |
| 6,891,311 B2 | 5/2005 | Phelps et al. |
| 6,894,426 B2 | 5/2005 | Shimizu |
| 6,899,682 B2 | 5/2005 | Eberle et al. |
| 6,919,668 B2 | 7/2005 | Nagahara et al. |
| 6,929,608 B1 | 8/2005 | Hutchinson et al. |
| 6,949,071 B1 | 9/2005 | Saied et al. |
| 6,962,567 B2 | 11/2005 | Eberle et al. |
| 6,974,417 B2 | 12/2005 | Lockwood et al. |
| 6,994,674 B2 | 2/2006 | Sheljaskow et al. |
| 7,017,245 B2 | 3/2006 | Baumgartner et al. |
| 7,052,460 B2 | 5/2006 | Liu et al. |
| 7,052,462 B2 | 5/2006 | Fukuda et al. |
| 7,087,970 B2 | 8/2006 | Nakamura |
| 7,091,125 B2 | 8/2006 | Werner et al. |
| 7,134,198 B2 | 11/2006 | Nakatani et al. |
| 7,139,676 B2 | 11/2006 | Barford |
| 7,148,607 B2 | 12/2006 | Sato |

| | | | |
|---|---|---|---|
| 7,148,608 B2 | 12/2006 | Baumgartner et al. | |
| 7,156,812 B2 | 1/2007 | Seward et al. | |
| 7,156,938 B2 | 1/2007 | Baumgartner et al. | |
| 7,208,717 B2 | 4/2007 | Partain et al. | |
| 7,230,368 B2 | 6/2007 | Lukacs et al. | |
| 7,255,678 B2 | 8/2007 | Mehi et al. | |
| 7,316,059 B2 | 1/2008 | Sato | |
| 7,391,872 B2 | 6/2008 | Pompei | |
| 7,424,771 B2 | 9/2008 | Shiraishi et al. | |
| 7,454,820 B2 | 11/2008 | Nakamura | |
| 7,459,836 B2 | 12/2008 | Scott | |
| 2001/0007940 A1 | 7/2001 | Tu et al. | |
| 2001/0041842 A1 | 11/2001 | Eberle et al. | |
| 2002/0000763 A1 | 1/2002 | Jones | |
| 2002/0050169 A1 | 5/2002 | Ritter et al. | |
| 2002/0058873 A1 | 5/2002 | Seward et al. | |
| 2002/0077551 A1 | 6/2002 | Fleischman et al. | |
| 2002/0130590 A1 | 9/2002 | Shiraishi et al. | |
| 2002/0157472 A1 | 10/2002 | Stephens et al. | |
| 2002/0173720 A1 | 11/2002 | Seo et al. | |
| 2003/0009873 A1 | 1/2003 | Hatangadi et al. | |
| 2003/0015037 A1 | 1/2003 | Stephens et al. | |
| 2003/0036702 A1 | 2/2003 | Davidsen | |
| 2003/0067249 A1 | 4/2003 | Lockwood et al. | |
| 2003/0073906 A1 | 4/2003 | Flesch et al. | |
| 2003/0127949 A1 | 7/2003 | Nagahara et al. | |
| 2003/0173870 A1 | 9/2003 | Simon Hsu | |
| 2003/0187356 A1 | 10/2003 | Wakabayashi et al. | |
| 2003/0189391 A1 | 10/2003 | Shimizu | |
| 2003/0205947 A1 | 11/2003 | Klee et al. | |
| 2004/0000841 A1 | 1/2004 | Phelps et al. | |
| 2004/0002656 A1 | 1/2004 | Sheljaskow et al. | |
| 2004/0011134 A1 | 1/2004 | Sato | |
| 2004/0040740 A1 | 3/2004 | Nakatani et al. | |
| 2004/0054289 A1 | 3/2004 | Eberle et al. | |
| 2004/0068191 A1 | 4/2004 | Seward et al. | |
| 2004/0071320 A1 | 4/2004 | Pfister | |
| 2004/0082858 A1 | 4/2004 | Fukuda et al. | |
| 2004/0111026 A1 | 6/2004 | Schoenfeld | |
| 2004/0122319 A1 | 6/2004 | Mehi et al. | |
| 2004/0176784 A1 | 9/2004 | Okada | |
| 2004/0236219 A1 | 11/2004 | Liu et al. | |
| 2005/0039323 A1 | 2/2005 | Sheljaskow | |
| 2005/0046030 A1 | 3/2005 | Nakamura | |
| 2005/0099096 A1 | 5/2005 | Baumgartner et al. | |
| 2005/0099097 A1 | 5/2005 | Baumgartner et al. | |
| 2005/0124894 A1 | 6/2005 | Puech | |
| 2005/0126490 A1 | 6/2005 | Hsieh et al. | |
| 2005/0156490 A1 | 7/2005 | Shiraishi et al. | |
| 2005/0197543 A1 | 9/2005 | Zan et al. | |
| 2005/0197574 A1 | 9/2005 | Eberle et al. | |
| 2005/0203402 A1 | 9/2005 | Angelsen et al. | |
| 2005/0240102 A1 | 10/2005 | Rachlin et al. | |
| 2005/0251043 A1 | 11/2005 | Saied et al. | |
| 2005/0251232 A1 | 11/2005 | Hartley et al. | |
| 2005/0272183 A1 | 12/2005 | Lukacs et al. | |
| 2006/0058681 A1 | 3/2006 | Eberle et al. | |
| 2006/0078501 A1 | 4/2006 | Goertz et al. | |
| 2006/0241446 A1 | 10/2006 | White et al. | |
| 2006/0241461 A1 | 10/2006 | White et al. | |
| 2007/0016071 A1 | 1/2007 | Eberle et al. | |
| 2007/0059247 A1 | 3/2007 | Lindner et al. | |
| 2007/0078347 A1 | 4/2007 | Srinivasan et al. | |
| 2007/0182287 A1 | 8/2007 | Lukacs et al. | |
| 2007/0200460 A1 | 8/2007 | Scott | |
| 2007/0205698 A1 | 9/2007 | Chaggares et al. | |
| 2007/0222339 A1 | 9/2007 | Lukacs et al. | |
| 2007/0239001 A1 | 10/2007 | Mehi et al. | |
| 2008/0015438 A1 | 1/2008 | Mehi et al. | |
| 2009/0240152 A1 | 9/2009 | Angelsen et al. | |
| 2009/0298299 A1 | 12/2009 | Cain et al. | |
| 2011/0144494 A1 | 6/2011 | Mehi et al. | |

FOREIGN PATENT DOCUMENTS

| | | | | |
|---|---|---|---|---|
| DE | 42 26 865 | 3/1994 | | |
| DE | 103 36 101 | 4/2004 | | |
| EP | 0 227 926 | 7/1987 | | |
| EP | 0 467 690 | 1/1992 | | |
| EP | 0 627 635 | 12/1994 | | |
| EP | 0 629 992 | 12/1994 | | |
| EP | 0 629 994 | 12/1994 | | |
| EP | 0 779 108 | 6/1997 | | |
| EP | 1 227 525 | 7/2002 | | |
| EP | 1 318 551 | 6/2003 | | |
| EP | 1 382 301 | 1/2004 | | |
| FR | 2 828 056 | 1/2003 | | |
| JP | 56-70000 | 6/1981 | | |
| JP | 01069094 A | * | 3/1989 | ............... 29/847 |
| JP | 2004-80193 | 3/2004 | | |
| WO | WO 97/17018 | 5/1997 | | |
| WO | WO 99/34733 | 7/1999 | | |
| WO | WO 99/45582 | 9/1999 | | |
| WO | WO 01/52437 | 7/2001 | | |
| WO | WO 02/43593 | 6/2002 | | |
| WO | WO 03/040427 | 5/2003 | | |
| WO | WO 2004/007098 | 1/2004 | | |
| WO | WO 2004/099814 | 11/2004 | | |
| WO | WO 2005/104210 | 11/2005 | | |
| WO | WO 2007/029028 | 3/2007 | | |
| WO | WO 2007/056104 | 5/2007 | | |
| WO | WO 2007/067282 | 6/2007 | | |

OTHER PUBLICATIONS

Brown et al., "Performance of a 50 MHz Annular Array Based Imaging System," *IEEE Ultrasonics Symposium* 760-763, 2004.

Brown et al., "In Vivo Assessment of Postnatal Murine Ocular Development by Ultrasound Biomicroscopy," *Current Eye Research* 30:45-51, 2005.

Brown et al., "Quantitation of Hemodynamic Function during Developmental Vascular Regression in the Mouse Eye," *Invest. Ophth. Vis. Sci.* 46:2231-2237, 2005.

Brown et al., "A Digital Beamformer for High-Frequency Annular Arrays," *IEEE Transactions on Ultrasonics, Ferroelectrics, and Frequency Control* 52:1262-1269, 2005.

Cannata et al., "Development of a High Frequency (35 MHz) Linear Ultrasonic Array Using 2-2 Composite Elements," *IEEE Ultrasonics Symposium* 894-897, 2004.

Ergun et al., "Broadband Capacitive Micromachined Ultrasonic Transducers Ranging From 10kHz to 60MHz for Imaging Arrays and More," *IEEE Ultrasonics Symposium* 1039-1043, 2002.

Farlow et al., "Micromachining of a Piezocomposite Transducer Using a Copper Vapor Laser," *IEEE Transactions on Ultrasonics, Ferroelectrics, and Frequency Control* 48:639-640, 2001.

Goertz et al., "High Frequency Nonlinear B-Scan Imaging of Microbubble Contrast Agents," *IEEE Transactions on Ultrasonics, Ferroelectrics, and Frequency Control* 52:65-79, 2005.

Guess et al., "Cross-talk Paths in Array Transducers," *IEEE Ultrasonics Symposium* 1279-1282, 1995.

Herman et al., "Advanced-laser Processing of Photonic and Microelectronic Components at Photonics Research Ontario," *SPIE Proc.* 3618:240-250, 1999.

Hu et al., "An FPGA Based Digital High Frequency Beamformer for Arrays," 8th Annual Fred S. Grodins Graduate Research Symposium, NIH Resource Center for Medical Ultrasound Transducer Technology, USC Los Angeles, CA, 84-85, 2004.

Hu et al., "FPGA Based Digital High Frequency Beamformers for Arrays," IEEE Ultrasonics Symposium 1347-1350, 2004.

Jensen et al., "A Program for Simulating Ultrasound Systems," *Medical & Biological Engineering & Computing* 34:351-354, 1996.

Lerch et al., "Simulation of Piezoelectric Devices by Two-and Three-Dimensional Finite Elements," *IEEE Transactions on Ultrasonics, Ferroelectrics, and Frequency Control* 37:233-247, 1990.

Liu et al., "Interdigital Pair Bonding for High Frequency (20-50MHz) Ultrasonic Composite Transducers," *IEEE Transactions on Ultrasonics, Ferroelectrics, and Frequency Control* 48:299-306, 2001.

Lukacs et al., "Laser Micromachined High Frequency Ultrasonic Arrays," *IEEE Ultrasonics Symposium* 1209-1212, 1999.

Lukacs et al., "Single Element and Linear Array PZT Ultrasound Biomicroscopy Transducers," *IEEE Ultrasonics Symposium* 1709-1712, 1997.

Lukacs et al., "Single Element and Linear Array Transducer Design for Ultrasound Biomicroscopy," *SPIE* 3341:272-282, 1998.

Lukacs, "Single Element and Linear Arrays High Frequency Ultrasonic Transducers Using PZT Sol Gel Composites," Ph.D. Thesis, Queen's University, 1-165, 1999.

McKeighen et al., "Design Guidelines for Medical Ultrasonic Arrays," *SPIE* 3341:2-18, 1998.

Michau et al., "Piezocomposite 30MHz Linear Array for Medical Imaging: Design Challenges and Performances Evaluation of a 128 Elements Array," *IEEE Ultrasonics Symposium* 898-901, 2004.

Oralkan et al., "Capacitive Micromachined Ultrasonic Transducers: Next-Generation Arrays for Acoustic Imaging?" *IEEE Trans. Ultrason. Ferroelectr. Freq. Control* 49:1596-1610, 2002.

Oralkan et al., "High-Frequency CMUT Arrays for High-Resolution Medical Imaging," *IEEE Ultrasonics Symposium*, 399-402, 2004.

Powell et al., "Incremental 'Model-Build-Test' Validation Exercise for a 1-D biomedical Ultrasonic Imaging Array," *IEEE Ultrasonics Symposium* 1669-1674, 1997.

Qi et al., "Finite Element Study on 1-D Array Transducer Design," *IEEE Trans. Ultrason. Ferroelectr. Freq. Control* 47:949-955, 2000.

Ritter et al., "A 30-MHz Piezo-Composite Ultrasound Array for Medical Imaging Applications," *IEEE Trans. Ultrason. Ferroelectr. Freq. Control.* 49:217-230, 2002.

Roh et al., "Finite Element Analysis on Reduction of the Cross Talk in Ultrasonic Transducers," *Proceedings of SPIE* 4693:214-221, 2002.

Sherrit et al., "Field Dependence of the Complex Piezoelectric, Dielectric, and Elastic Constants of Motorola PZT 3203 HD Ceramic," *SPIE* 3040:99-109, 1997.

Snook et al., "Design of a 50 MHz Annular Array Using Fine-Grain Lead Titanate," *Proceedings of SPIE* 4687:91-98, 2002.

Tutwiler et al., "Design of a Test System to Characterize Very High-Frequency Ultrasound Transducer Arrays," *SPIE* 3664:182-193, 1999.

Villaneuva et al., "Microbubbles Targeted to Intercellular Adhesion Molecule-1 Bind to Activation Coronary Artery Endothelial Cells," *Circulation* 98:1-5, 1998.

Wang et al., "Passive Materials for High Frequency Ultrasound Transducers," *SPIE* 3664:35-42, 1999.

Wu et al. "Design of an Analogy Beamformer for Very High-Frequency Ultrasound Transducer Arrays," *Proceedings of SPIE* 3982:142-149, 2000.

International Search Report for PCT/CA2009/001363, mailed on Feb. 19, 2009.

Written Opinion of the International Searching Authority for PCT/CA2009/001363, mailed on Feb. 19, 2009.

Statement of Sale Prior to Apr. 2003.

\* cited by examiner

FIG. 11A
FIG. 11B
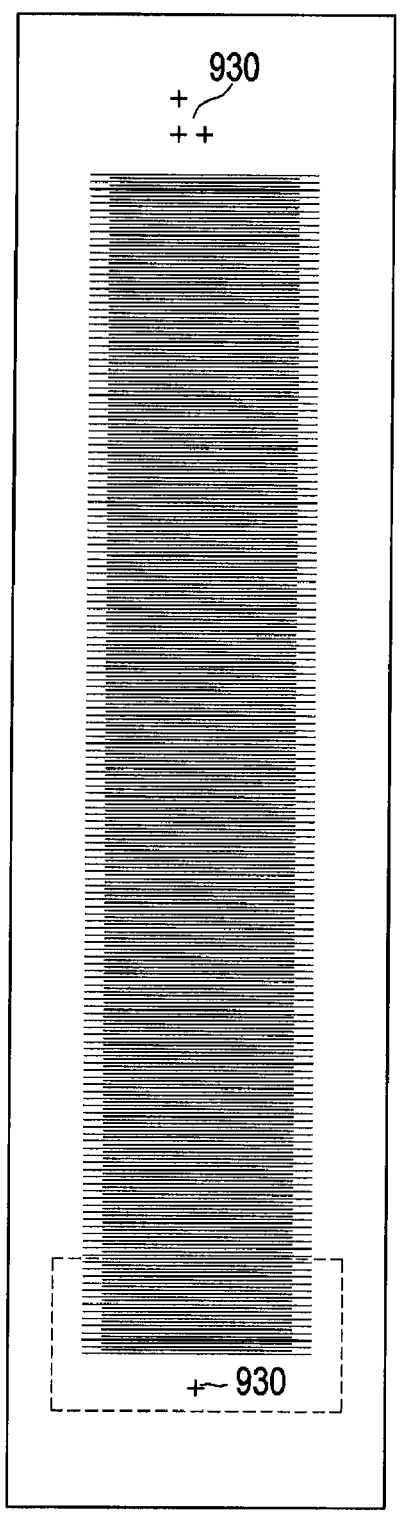
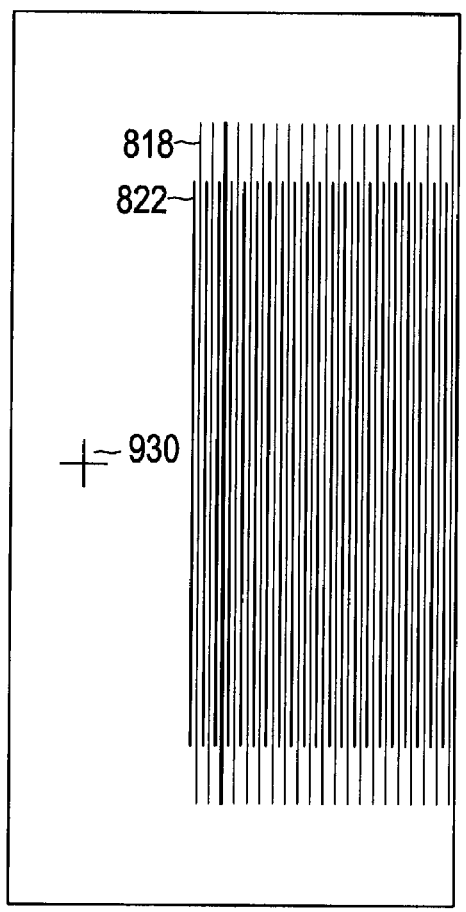

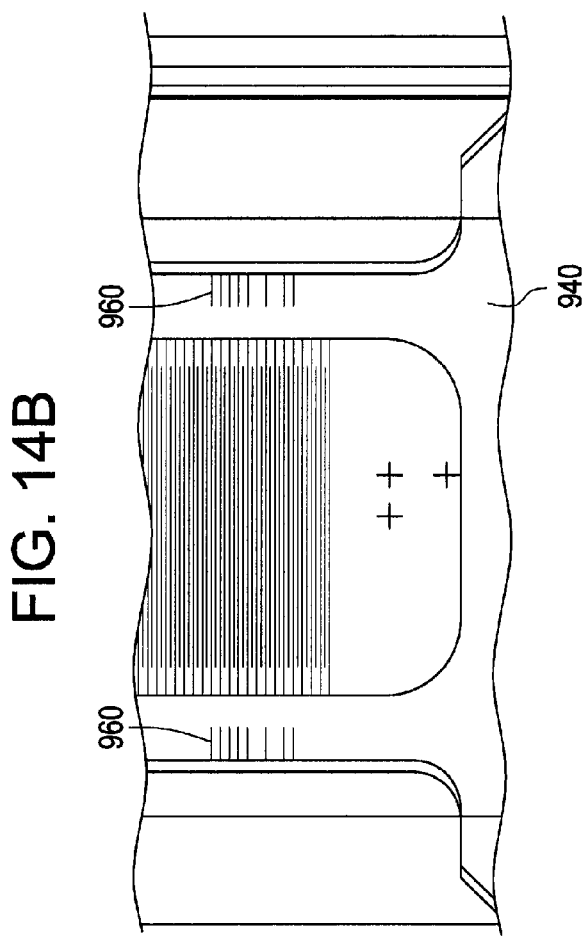
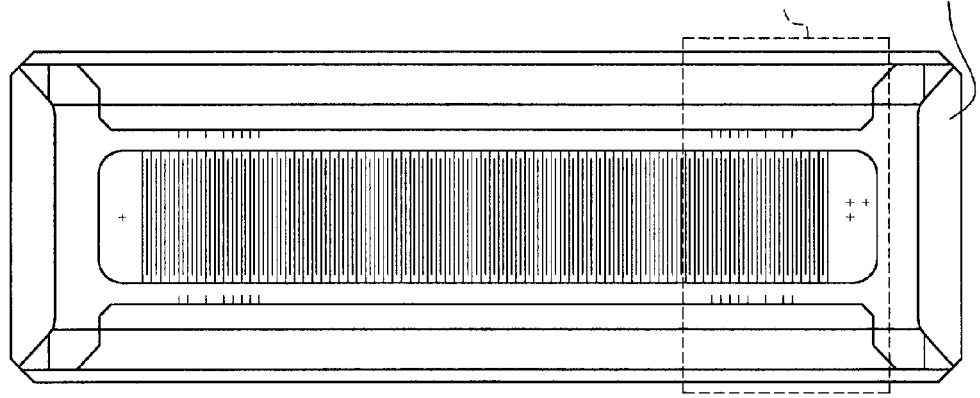

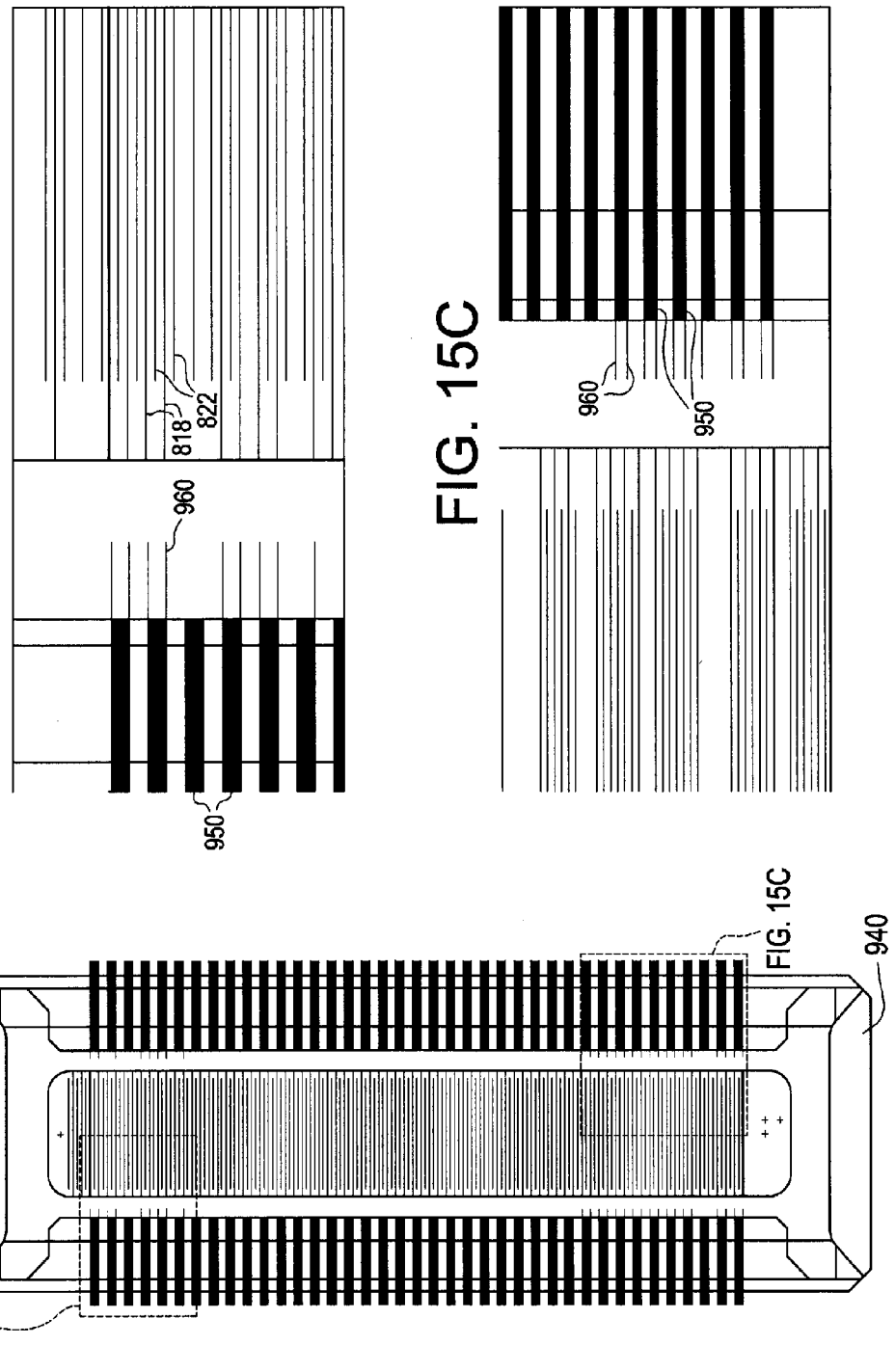

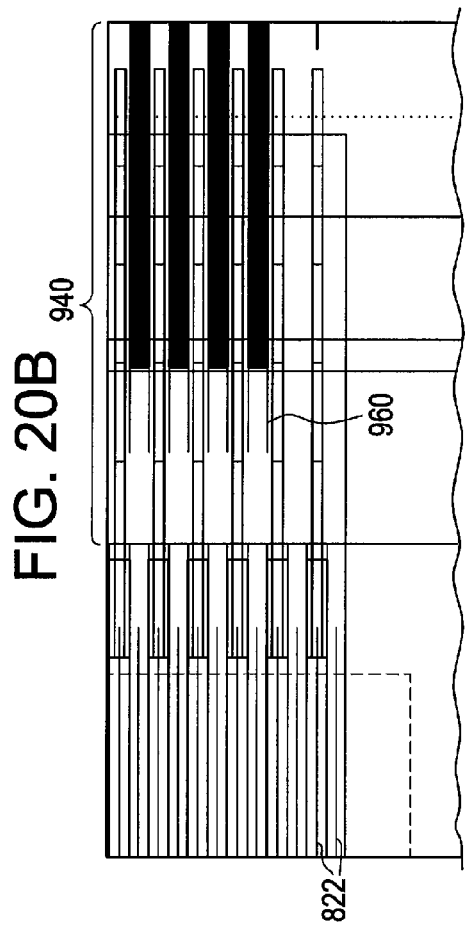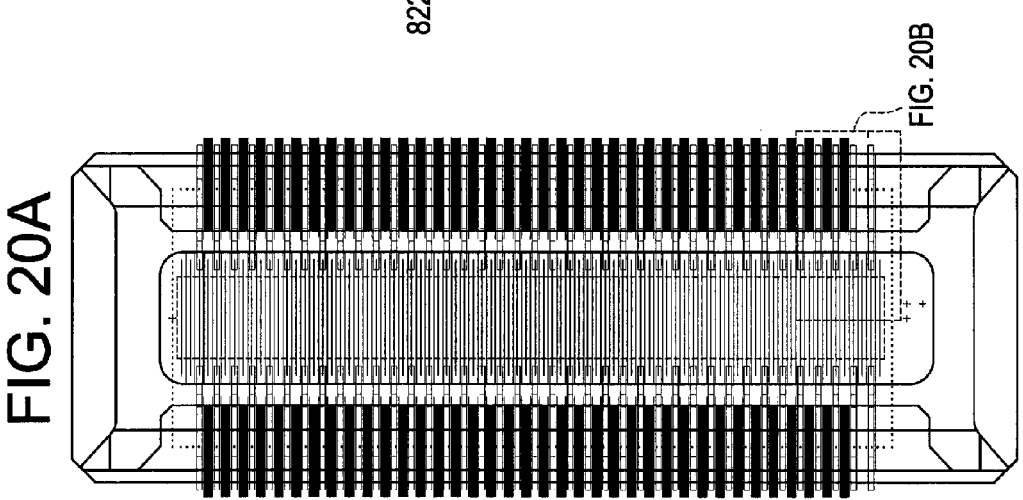

METHODS FOR MANUFACTURING ULTRASOUND TRANSDUCERS AND OTHER COMPONENTS

CROSS-REFERENCE TO RELATED APPLICATIONS

This application claims benefit of U.S. Provisional Application No. 61/192,661 and 61/192,690, both filed on Sep. 18, 2008 and both of which are hereby incorporated by reference.

FIELD OF THE INVENTION

The invention relates to the fields of manufacture of electrical components such as ultrasound transducers.

SUMMARY OF THE INVENTION

In general, the invention provides methods for manufacturing electrical components, such as arrayed ultrasonic transducers.

In one aspect, the invention features a method for producing electrodes in a pattern by providing an electrical component having a first plurality of electrodes; placing a connector having a second plurality of electrodes in proximity to the electrical component; depositing a composite dielectric material including a matrix material and a particulate material on the first plurality of electrodes and the second plurality of electrodes, wherein the matrix material is laser ablated at a lower fluence than the particulate material; laser ablating at least a portion of the composite dielectric material to remove matrix material and increase the surface area of the composite dielectric material; laser ablating the composite dielectric material to expose the first plurality of electrodes and the second plurality of electrodes; and laser ablating a trench in the composite dielectric material from each of the first plurality of electrodes to a corresponding electrode of the second plurality; depositing a conductive metal on the ablated areas; depositing a resist on the conductive metal, wherein the resist is thicker over the first and second pluralities of electrodes and the trenches compared to other ablated areas; and removing a portion of the resist to expose a portion of the conductive metal in a negative pattern and etching the exposed portion of the conductive metal to produce the electrodes in the pattern. The method may further include laser ablating the areas of etched conductive metal to remove at least a portion of the composite dielectric material therein. In this optional step, substantially all of the composite dielectric material and a portion of the component lying under the areas of etched conductive metal may be ablated.

In a related aspect, the invention features a method for producing electrodes in a pattern by providing an ultrasound array transducer stack having a piezoelectric layer and a plurality of first kerf slots that extend a predetermined depth therein the stack, and wherein the plurality of first kerf slots define a plurality of ultrasonic array elements; placing a connector having an electrical connection for each of the plurality of array elements in proximity to the stack; depositing a composite dielectric material including a matrix material and a particulate material on the bottom surface of the stack and a portion of the connector, wherein the matrix material is laser ablated at a lower fluence than the particulate material; laser ablating at least a portion of the composite dielectric material to remove matrix material and increase the surface area of the composite dielectric material; laser ablating the composite dielectric material to expose the plurality of array elements; and laser ablating a trench in the composite dielectric material from each array element to one electrical connection in the connector, wherein the ablating does not expose the plurality of first kerf slots; depositing a conductive metal on the ablated areas; depositing a resist on the conductive metal, wherein the resist is thicker over each array element and trench compared to the plurality of first kerf slots; and removing a portion of the resist to expose a portion of the conductive metal in a pattern that is the negative of that of the electrodes and etching the exposed portion of the conductive metal to produce the electrodes in the pattern. This method may further include laser ablating the areas of etched conductive metal to remove the composite dielectric material over the plurality of first kerf slots to create a depression between individual array elements. In this embodiment, the first kerf slots may be filled with a solid material, such as epoxy. The method may also include laser ablating the depressions between individual array elements, wherein the subsequent ablation of the depression occurs at a higher fluence than that used to create the depressions. The method may further include removing the resist from the patterned electrodes. The method may include a further etching step to remove conductive metal burs produced by laser ablation. Preferably, no step occurs at higher than 70° C. The method may also include depositing an adhesion layer, e.g., including chromium, prior to the conductive metal, e.g., gold. The etching step may remove the conductive metal deposited on the adhesion layer, while the laser ablation of the composite material may also remove the adhesion layer exposed by etching. Preferably, the resist is removed by ablation at a fluence insufficient to ablate the conductive metal. The pitch of the plurality of array elements is preferably at most 100 µm, e.g., at most 65 µm. An exemplary matrix material in the composite dielectric material is epoxy, and exemplary particular materials are silica and silicon carbide.

The invention further features an ultrasound transducer produced by the above method. Such a transducer includes an array transducer stack having a plurality of first kerf slots that extend a predetermined depth therein the stack, and wherein the plurality of first kerf slots define a plurality of ultrasonic array elements; a connector having an electrode for each array element; and a composite dielectric material including a matrix material and a particulate material on the bottom surface of the stack and a portion of the connector, wherein the matrix material is laser ablated at a lower fluence than the particulate material, wherein the composite dielectric material is disposed over a portion of the bottom surface of the stack and the connector; wherein a trench in the composite dielectric material connects each array element to one of the electrodes of the connector; and wherein a metal deposited in each trench provides an electrical connection between each active element and one of the electrodes of the connector. The plurality of first kerf slots are optionally filled with a solid material, and the bottom surface of the stack comprises depressions in the solid material. The transducer may further include a backing layer disposed over at least portion of the composite dielectric material, the trenches, and each array element. The transducer may also include a matching layer attached to the top surface of the stack and/or a lens attached to the top surface of the stack. The array elements typically operate at a center frequency of at least 20 MHz. The composite dielectric layer may also be sloped adjacent to each of the array elements to provide apodization and to suppress side lobes in elevation. The transducer may also include a plurality of second kerf slots defined therein the piezoelectric stack, each second kerf slot extending a predetermined depth therein the stack, wherein each second kerf slot is positioned adjacent to at least one first kerf slot and the plurality of second kerf slots define a plurality of array sub-elements.

In another aspect, the invention features a method of forming an ultrasonic matching layer by providing an acoustic array transducer stack comprising a piezoelectric layer and having a top surface and a plurality of array elements, wherein the top surface includes a plurality of spacers not disposed over the plurality of array elements; providing a lens assembly having a top surface and a bottom surface; contacting the bottom surface of the lens assembly with the plurality of spacers; and curing an adhesive between the top surface of the transducer stack and the bottom surface of the lens assembly to form the ultrasound matching layer, wherein the adhesive bonds to the bottom surface of the lens assembly and the top surface of the transducer stack, and the distance between the top surface of the transducer stack and the bottom surface of the lens assembly resulting from the plurality of spacers is appropriate for an ultrasound matching layer. The lens assembly may include a lens, e.g., of Rexolite or TPX, and a second matching layer, e.g., including cyanoacrylate, forming the bottom surface of the assembly. The second matching layer may adhere directly to the lens. The transducer stack may further include a plurality of first kerf slots that extend a predetermined depth therein the stack, and wherein the plurality of first kerf slots define the plurality array elements. The transducer stack may also include third and fourth matching layers disposed between the piezoelectric layer and the matching layer produced.

In a related aspect, the invention features an ultrasound transducer including a lens assembly having a top and bottom surface, an array transducer stack having a top and bottom surface, and a matching layer adhering to the bottom surface of the lens assembly and the top surface of the transducer stack, wherein the transducer stack includes a piezoelectric layer and a plurality of array elements, the top surface of the transducer stack comprises a plurality of spacers not disposed over the plurality of array elements, and the bottom of the lens assembly contacts the plurality of spacers. The transducer stack may further include a plurality of first kerf slots that extend a predetermined depth therein the stack, and wherein the plurality of first kerf slots define the plurality array elements and optionally a plurality of second kerf slots defined therein the piezoelectric stack, each second kerf slot extending a predetermined depth therein the stack, wherein each second kerf slot is positioned adjacent to at least one first kerf slot and the plurality of second kerf slots define a plurality of array sub-elements. The lens assembly may include a lens, e.g., of Rexolite or TPX, and a second matching layer, e.g., including cyanoacrylate, forming the bottom surface of the assembly. The second matching layer may adhere directly to the lens. The transducer stack may also include third and fourth matching layers disposed between the piezoelectric layer and the matching layer adhering to the bottom surface of the lens assembly. The array elements preferably operate at a center frequency of at least 20 MHz. The transducer may also include a connector having an electrode for each array element and a composite dielectric material comprising a matrix material and a particulate material on the bottom surface of the stack and a portion of the connector, wherein the matrix material is laser ablated at a lower fluence than the particulate material, wherein the composite dielectric material is disposed over a portion of the bottom surface of the stack and the connector; wherein a trench in the composite dielectric material connects each array element to one of the electrodes of the connector; and wherein a metal deposited in each trench provides an electrical connection between each active element and one of the electrodes of the connector.

In another aspect, the invention features, a method of depositing a material, e.g., metal or adhesive, on a surface by providing a composite dielectric substrate comprising a matrix material, e.g., a polymer such as epoxy, and a particulate material, e.g., silica or silicon carbide; laser ablating a surface of the composite substrate at a fluence sufficient to ablate the matrix materials but not the particulate material to form an ablated surface having greater surface area than the surface of the composite substrate; and depositing the material on the ablated surface, wherein the strength of adhesion of the material to the ablated substrate is great than that of the material to the unablated substrate. An exemplary metal for deposition is gold, and the method may further include applying an adhesion layer prior to depositing the gold.

Advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

FIGS. 11A and 11B are a schematic view and a magnified schematic view of an exemplary kerf pattern to be machined into the PZT stack. In this aspect, the longer lines are representative of the first kerf slots between array elements, and the shorter lines are representative of the second kerf slots, i.e., the sub-dice kerfs.

FIGS. 14A and FIG. 14B are a schematic bottom plan view and a magnified schematic bottom plan view of the support member with the PZT stack fixedly mounted therein showing flex alignment features laser cut into the support structure and positioned with respect to the respective array kerfs. In one aspect, the flex alignment features on the right are offset relative to the features on the left by a distance substantially equal to the pitch of the array. An enlarged top plan view is also shown.

FIG. 15A-15C are a schematic bottom plan view and magnified schematic bottom plan views of the support member with the PZT stack fixedly mounted therein showing how the flex circuit pair is aligned with respect to the array kerfs. The black bars represent the copper traces on the top side of the flex circuit.

FIG. 20A and 20B are a schematic view and a magnified schematic view of the full signal electrode pattern for an exemplary 256 element transducer. The dashed lines indicate the active area of the PZT stack and the dotted lines indicate the perimeter of the blanket signal electrode. The laser trimming (black lines) extends beyond the Au perimeter such that each signal electrode is isolated.

FIG. 22A represents the array assembly before the ground connection to the flex circuits has been made, and FIG. 22B represents the array assembly after the ground connection has been made such that the signal return path is completed.

DETAILED DESCRIPTION OF THE INVENTION

Figure 1:
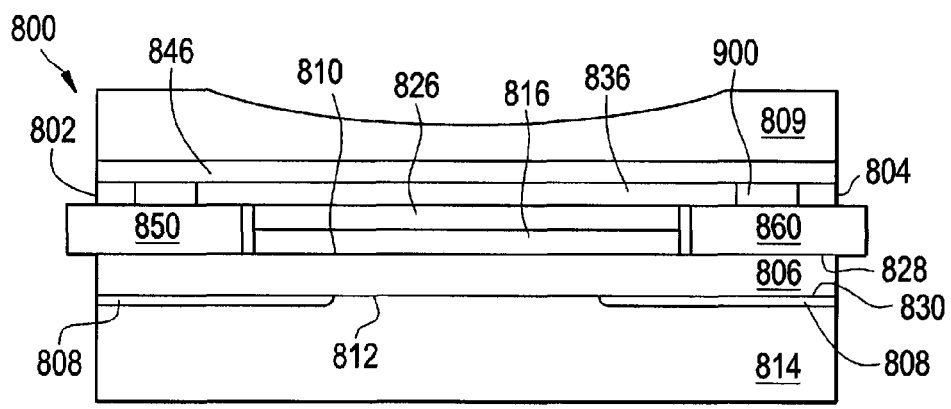
FIG. 1 is a cross-sectional view of an exemplary schematic piezoelectric stack (not to scale), showing a PZT layer, a ground electrode layer mounted to a portion of the top surface of the PZT layer and extending outwardly beyond the longitudinal edges of the PZT layer, a first and a second matching layer mounted on a portion of the top surface of the ground electrode layer, a lens, a fourth matching layer mounted to the bottom surface of the lens, a third matching layer mounted to a portion of the top surface of the second matching layer and the bottom of the fourth matching layer, and a dielectric layer underlying the inactive area of the transducer. Further showing a plurality of spacers formed thereon the top surface of the ground electrode layer that extend upwardly a predetermined distance relative to the top surface of the PZT layer such that the bottom surface of the fourth matching layer can be positioned at a desired distance relative to the PZT layer and the intervening first and second matching layers.
Figure 2:
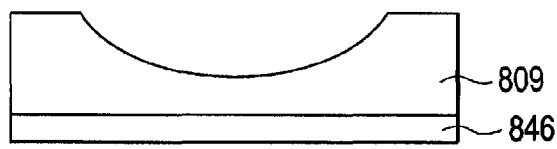
FIG. 2 is a schematic cross-sectional view of an exemplary lens with a focal length of 10 mm (R=3.65mm), a total height of 0.45 mm, and center thickness of 0.25 mm, including the lens and the fourth matching layer (not to scale).

The invention features methods for the manufacture of electrical components such as ultrasound transducers. In particular, the invention provides methods of depositing materials, such as metals, on surfaces; methods of patterning electrodes, e.g., in the connection of an ultrasound transducer to an electrical circuit; and methods of making integrated matching layer for an ultrasound transducer. The invention also features ultrasound transducers produced by the methods described herein.

Deposition of Materials

The invention provides improved methods for the adhesion of materials to a surface, e.g., a thin film of metal or an adhesive such as epoxy. The method involves use of a substrate of a composite material. The composite material includes a matrix material and a particulate material, and the matrix material ablates at a lower laser fluence than the particulate material. When this substrate is ablated at an appropriate fluence, the matrix material is removed, but the particulate material is retained unless all matrix material surrounding the particles is removed. The result of the process is a highly three-dimensional surface formed by a combination of the matrix and partially exposed particulate material. The surface area of the new morphology is greatly increased compared to the unablated surface. A material, such as a metal or adhesive, is then deposited onto the ablated surface, and adhesion is increased because of the morphology created by ablation. The improved adhesion preferably allows for later ablation of the material in selected areas without delamination of the material in unablated areas. An exemplary matrix material is a polymer such as epoxy, and exemplary particulate materials are silica and silicon carbide. An exemplary metal for deposition is gold. An adhesion layer, e.g., containing chromium, may also be deposited for certain metals, such as gold, as is known in the art. Examples of conditions and uses of the method are provided herein.

Patterning of Electrodes

The invention also provides a method for patterning electrodes. This process can be used to connect any electrical component that can withstand the metallization step (highest temp ~60-70° C.) directly to a flex or other circuit board type component. This method can be used to create features smaller than 5 µm over mm scale distances in X, Y, and Z.

In general, the method involves providing an electrical component needing the patterning of electrodes. The component is coated with a material, such as the composite material described above. This coating is generally ablated and selectively removed in the desired pattern of the electrodes. A conductive metal layer is then deposited over the ablated surface. A resist is then applied over the metal layer. Because the coating was removed in the pattern of the electrodes, the metal applied where the coating is removed is deposited in a trough or trench. These troughs or trenches are filled with resist, resulting in a thicker layer of resist overtop of the pattern of the electrodes. The resist is then removed from areas not forming part of the electrode pattern, and the metal is etched. Any remaining metal and the coating in these areas is then ablated. Finally, the resist may be removed, resulting in the electrode pattern. As is described in more detail herein, a portion of the electrical component, e.g., filler material in a kerf slot of a transducer, may be ablated to create a depression relative to the patterned electrodes. Ablation at relatively high fluence in these depressions may then be employed to remove extraneous metal left behind by previous steps. The depression protects the patterned electrodes from the byproducts of ablation, which would otherwise likely result in delamination.

An exemplary use of the method is in making electrical connections to an arrayed ultrasound transducer. Each element of an array is typically connected to a coaxial cable. At high frequencies (e.g., 20 MHz and up), the elements making up the array are typically too small and fragile for conventional wire bonding (which usually needs at least about 75 µm). In addition, thermal budgets required for wire bonding may also be problematic. For high frequency transducers, wet etching may also be ineffective because of the inability to hard bake resist because of thermal budgets, as the resist may dissolver prior to removal of the metal. Laser ablation of the electrode may also be problematic, as thin films cab be removed, but frequently crack, and thicker films (>about 6000 Angstroms) providing crack resistance are prone to shorting because of splattering of metal during laser ablation. Also, the ablation process may cause collateral damage of the electrode. The method of invention, however, may be employed to make electrical connections with elements of an array, e.g., with a pitch of 40 µm or less (e.g., less than 25 µm) and sub elements as small as 16 µm wide.

A laser that can be used for ablation in conjunction with the invention is a short wavelength laser such as a KrF Excimer laser system (having, for example, about a 248 nm wavelength or an argon fluoride laser (having, for example, about a 193 nm wavelength). In another aspect, the laser used to cut the piezoelectric layer is a short pulse length laser. For example, lasers modified to emit a short pulse length on the order of ps to fs can be used. A KrF excimer laser system (UV light with a wavelength of about 248 nm) with a fluence range of about and between 0-20 J/cm$^2$ can be employed. Resist may be removed at a fluence below that required to remove the conductive material (e.g., less than 0.8 J/cm$^2$). When it is desired to remove residual conductive metal, adhesion layers, and the composite material as described herein by ablation, the fluence may be between 0.8 to 1.0 J/cm$^2$. Ablation at higher fluences, e.g., up to 5 J/cm$^2$, may be employed to remove composite material (and underlying portions of an electrical component) located in depressions.

Further examples of conditions and uses of the method are provided herein.

Integrated Matching Layer

The invention also features a process for making an integrated matching layer. For high frequency applications, a lens for focusing an ultrasound array is often manufactured as a separate part, which must be attached to the transducer. At high frequencies, the use of adhesives to attached the lens is complicated by the need to reduce any bondline to less than approximately 1 µm for 20 MHz and thin for higher frequencies. Producing such bondlines presents challenges as follows: i) large voids are created, when a small generally spherical void in the adhesive is squeezed flat. Such voids can result from wetting issues on either surface or from small trapped voids in the adhesive. ii) Squeezing the bondline to such dimensions can interfere with the mobility of the molecules in the adhesive and compromise performance. iii) In order to press a bondline to the appropriate dimension, surplus adhesive must be squeezed out from in between the two parts being bonded. As the thickness of the bond decreases, the force required to overcome shear forces within the adhesive increases nonlinearly with the bond thickness and can quickly exceed acceptable force budgets for the stack and/or lens materials. In order to ensure that the bondline has no negative impact on the stack, the invention provides a method of making the bondline into a matching layer. This approach eliminates the need for an ultra thin layer and thus removes the concerns listed above.

The method employs spacers applied around the perimeter of the transducer, and then lapped to the desired final height of the integral matching layer. The matching layer is then made by curing the adhesive between the lens (and any matching layers attached to the lens) and the surface to which the spacers are attached. If particles are employed in the adhesive, e.g., to adjust the acoustical impedance, nano-particle dopants may be employed to ensure that the resulting uncured glue can be pressed down onto the spacers without more than a fraction of a micron error (due to particles being trapped between the top of the spacers, and the bottom of the lens). Spacers are desirably small to minimize trapping of powder, but large enough to be accurately lapped to height, e.g., about 0.25 to 0.75 mm in diameter. The clamping force required for this process is minimal, as the bondline is relatively thick, e.g., between 5 and 25 µm) in the desired frequency range. Examples of conditions and uses of the method are provided herein.

General Description of a Transducer

The invention will be further described with respect to ultrasound transducers that can be produce with the methods described herein. Components of the transducer stack, including piezoeletric layers, matching layers, lenses, and backing layers are known in the art and described in U.S. Pat. No. 7,230,368, U.S. Publication No. 2007/0222339, U.S. Publication No. 2007/0205698, and U.S. Publication No. 2007/0205697.

In one aspect, an ultrasonic transducer includes a stack having a first face, an opposed second face, and a longitudinal axis Ls extending between. The stack includes a plurality of layers, each layer having a top surface and an opposed bottom surface. In one aspect, the plurality of layers of the stack includes a piezoelectric layer and a dielectric layer (which may be deposited and patterned as described herein). In one aspect, the dielectric layer is connected to and underlies at least a portion of the piezoelectric layer.

The plurality of layers of the stack can further include a ground electrode layer, a signal electrode layer, a backing layer, and at least one matching layer. Additional layers cut can include, but are not limited to, temporary protective layers (not shown), an acoustic lens, photoresist layers (not shown), conductive epoxies (not shown), adhesive layers (not shown), polymer layers (not shown), metal layers (not shown), and the like.

The piezoelectric layer can be made of a variety of materials. For example, materials that form the piezoelectric layer include ceramic, single crystal, polymer and co-polymer materials, ceramic-polymer and ceramic-ceramic composites with 0-3, 2-2 and/or 3-1 connectivity, and the like. In one example, the piezoelectric layer includes lead zirconate titanate (PZT) ceramic.

The dielectric layer can define the active area of the piezoelectric layer. The dielectric layer can be applied to the bottom surface of the piezoelectric layer. In one aspect, the dielectric layer does not cover the entire bottom surface of the piezoelectric layer. In one aspect, the dielectric layer defines an opening or gap that extends a second predetermined length in a direction substantially parallel to the longitudinal axis of the stack. The opening in the dielectric layer is preferably aligned with a central region of the bottom surface of the piezoelectric layer. The opening defines the elevation dimension of the array. In one aspect, each element of the array has the same elevation dimension, and the width of the opening is constant within the area of the piezoelectric layer reserved for the active area of the device that has formed kerf slots. In one aspect, the length of the opening in the dielectric layer can vary in a predetermined manner in an axis substantially perpendicular to the longitudinal axis of the stack resulting in a variation in the elevation dimension of the array elements.

The relative thickness of the dielectric layer and the piezoelectric layer and the relative dielectric constants of the dielectric layer and the piezoelectric layer define the extent to which the applied voltage is divided across the two layers. In one example, the voltage can be split at 90% across the dielectric layer and 10% across the piezoelectric layer. It is contemplated that the ratio of the voltage divider across the dielectric layer and the piezoelectric layer can be varied. In the portion of the piezoelectric layer where there is no underlying dielectric layer, then the full magnitude of the applied voltage appears across the piezoelectric layer. This portion defines the active area of the array. In this aspect, the dielectric layer allows for the use of a piezoelectric layer that is wider than the active area and allows for kerf slots to be made in the active area and extend beyond this area in such a way that array elements and array sub-elements are defined in the active area, but a common ground is maintained on the top surface.

A plurality of first kerf slots are defined therein the stack. Each first kerf slot extends a predetermined depth therein the stack and a first predetermined length in a direction substantially parallel to the longitudinal axis of the stack. The "predetermined depth" of the first kerf slot may follow a predetermined depth profile that is a function of position along the respective length of the first kerf slot. The first predetermined length of each first kerf slot is at least as long as the second predetermined length of the opening defined by the dielectric layer and is shorter than the longitudinal distance between the first face and the opposed second face of the stack in a lengthwise direction substantially parallel to the longitudinal axis of the stack. In one aspect, the plurality of first kerf slots define a plurality of ultrasonic array elements.

The ultrasonic transducer can also comprise a plurality of second kerf slots. In this aspect, each second kerf slot extends a predetermined depth therein the stack and a third predetermined length in a direction substantially parallel to the longitudinal axis of the stack. The "predetermined depth" of the second kerf slot can follow a predetermined depth profile that is a function of position along the respective length of the second kerf slot. The length of each second kerf slot is at least as long as the second predetermined length of the opening defined by the dielectric layer and is shorter than the longitudinal distance between the first face and the opposed second face of the stack in a lengthwise direction substantially parallel to the longitudinal axis of the stack. In one aspect, each second kerf slot is positioned adjacent to at least one first kerf slot. In one aspect, the plurality of first kerf slots define a plurality of ultrasonic array elements and the plurality of second kerf slots define a plurality of ultrasonic array sub-elements. For example, an array with one second kerf slot between two respective first kerf slots has two array sub-elements per array element. For a 64-element array with two sub-diced elements per array element, 129 respective first and second kerf slots are made to produce 128 piezoelectric sub-elements that make up the 64 elements of the array. It is contemplated that this number can be increased for a larger array. For an array without sub-dicing, 65 and 257 first kerf slots can be used for array structures with 64 and 256 array elements respectively. In one aspect, the first and/or second kerf slots can be filled with air. In an alternative aspect, the first and/or second kerf slots can also be filled with a liquid or a solid, such as, for example, a polymer.

Because neither the first or second kerf slots extend to either of the respective first and second faces of the stack, i.e., the kerf slots have an intermediate length, the formed array elements are supported by the contiguous portion of the stack near the respective first and second faces of the stack.

The piezoelectric layer of the stack can resonate at frequencies that are considered high relative to current clinical imaging frequency standards. In one aspect, the piezoelectric layer resonates at a center frequency of about 30 MHz. In other aspects, the piezoelectric layer resonates at a center frequency of about and between 10-200 MHz, preferably about and between, 20-150 MHz, and more preferably about and between 25-100 MHz.

Each of the plurality of ultrasonic array sub-elements has an aspect ratio of width to height of about and between 0.2-1.0, preferably about and between 0.3-0.8, and more preferably about and between 0.3-0.7. In one aspect, an aspect ratio of width to height of less than about 0.6 for the piezoelectric elements can be used. This aspect ratio, and the geometry resulting from it, helps to separate lateral resonance modes of an array element from the thickness resonant mode used to create the acoustic energy. Thus, the noted width to height ratios are configured to prevent any lateral resonant modes within the piezoelectric bar from interfering with the dominant thickness mode resonance. Similar cross-sectional designs can be considered for arrays of other types as understood by one skilled in the art. Each array element can comprise at least one sub-dice kerf, such that each array element will effectively include two or more bars, in which the signal electrodes for all bars of each respective element are electrically shorted together.

The width to height aspect ratio of the piezoelectric bar can also impact the directivity of the array element, i.e., the more narrow the width, the lower the directivity and the larger the steering angle of the array. For arrays with a pitch greater than about 0.5 lambda, the amplitude of the grating lobes produced for an aperture of driven elements will increase. Without limitation, various exemplary width/height aspect ratios of PZT bars can include:

| Approx Frequency Range | Pitch (µm) | PZT (µm) | Kerf (µm) | W/H |
| --- | --- | --- | --- | --- |
| 13-24 MHz | 90 | 75 | 10 | 0.53 |
| 18-42 MHz | 75 | 51 | 8 | 0.58 |
| 18-42 MHz | 60 | 45 | 5 | 0.55 |
| 22-55 MHz | 55 | 39 | 5 | 0.58 |
| 22-55 MHz | 55 | 39 | 5 | 0.58 |
| 30-70 MHz | 38 | 25 | 3-4 | 0.56 |

The first and/or second kerf slots can be filled with air or with a liquid or a solid, such as a polymer. The filler can be a low acoustic impedance material that minimizes mechanical coupling between adjacent piezoelectric bars within the array structure. If selected, the low acoustic impedance material can have an acoustic response that is outside of the bandwidth of the piezoelectric bars to avoid any unwanted coupling with the piezoelectric bars. It will be appreciated that the choice of filler can influence the effective width of an array element, i.e., the effective width of the array element will be equal to, or larger than, the actual width of the array element due to any mechanical coupling between elements. Further, as the effective width increases, the directivity of the array element will increase slightly. For example, and not meant to be limiting, Epotek 301 and/or 301-2 epoxies, and the like, can be used as kerf filler materials.

The formation of sub-elements by "sub-dicing," using a plurality of first and second kerf slots is a technique in which two adjacent sub-elements are electrically shorted together, such that the pair of shorted sub-elements act as one element of the array. For a given element pitch, which is the center to center spacing of the array elements resulting from the first kerf slots, sub-dicing allows for an improved element width to height aspect ratio such that unwanted lateral resonances within the element are shifted to frequencies outside of the desired bandwidth of the operation of the device.

In one aspect, the piezoelectric layer of the stack has a pitch of about and between 7.5-300 microns, preferably about and between 10-150 microns, and more preferably about and between 15-100 microns. In one example and not meant to be limiting, for a 30 MHz array design, the resulting pitch for a 1.5λ is about 74 microns.

At high frequencies, when the width of the array elements and of the kerf slots scale down to the order of 1-10's of microns, it is desirable in array fabrication to make narrow kerf slots. Narrowing the kerf slots can minimize the pitch of the array such that the effects of grating lobes of energy can be minimized during normal operation of the array device. Further, by narrowing the kerf slots, the element strength and sensitivity are maximized for a given array pitch by removing as little of the piezoelectric layer as possible. Using laser machining, the piezoelectric layer may be patterned with a fine pitch and maintain mechanical integrity.

As noted above, the plurality of layers can further include a signal electrode layer and a ground electrode layer. The electrodes can be defined by the application of a metallization layer that covers the dielectric layer and the exposed area of the piezoelectric layer. The electrode layers can comprise any metalized surface as would be understood by one skilled in the art. A non-limiting example of electrode material that can be used is Nickel (Ni). A metalized layer of lower resistance (at 1-100 MHz) that does not oxidize can be deposited by thin film deposition techniques such as sputtering (evaporation, electroplating, etc.). A Cr/Au combination (300/3000 Angstroms respectively) is an example of such a lower resistance metalized layer, although thinner and thicker layers can also be used. The Cr is used as an interfacial adhesion layer for the Au. As would be clear to one skilled in the art, it is contemplated that other conventional interfacial adhesion layers well known in the semiconductor and microfabrication fields can be used. Signal electrodes can be patterned as described herein.

The plurality of layers of the stack can further include at least one matching layer having a top surface and an opposed bottom surface. In one aspect, the plurality of layers includes two such matching layers. At least a portion of the bottom surface of the first matching layer can be connected to at least a portion of the top surface of the piezoelectric layer. If a second matching layer is used, at least a portion of the bottom surface of the second matching layer is connected to at least a portion of the top surface of the first matching layer. The matching layer(s) can be at least as long as the second predetermined length of the opening defined by the dielectric layer in a lengthwise direction substantially parallel to the longitudinal axis of the stack. Methods for producing integrated matching layers are described herein.

The matching layer(s) can have a thickness that is usually equal to about or around ¼ of a wavelength of sound, at the center frequency of the device, within the matching layer material itself. The specific thickness range of the matching layers depends on the actual choice of layers, their specific material properties, and the intended center frequency of the device. In one example and not meant to be limiting, for polymer based matching layer materials, and at 30 MHz, this results in a preferred thickness value of about 15-25 µm.

In one aspect, the acoustic impedance of a matching layer can be between 8-9 Mrayl; in another aspect, the impedance can be between 3-10 Mrayl; and, in yet another aspect, the impedance can be between 1-33 Mrayl.

The plurality of layers of the stack can further include a backing layer having a top surface and an opposed bottom surface. In one aspect, the backing layer substantially fills the opening defined by the dielectric layer. In another aspect, at least a portion of the top surface of the backing layer is connected to at least a portion of the bottom surface of the dielectric layer. In a further aspect, substantially all of the bottom surface of the dielectric layer is connected to at least a portion of top surface of the backing layer. In yet another aspect, at least a portion of the top surface of the backing layer is connected to at least a portion of the bottom surface of the piezoelectric layer.

The matching and backing layers can be selected from materials with acoustic impedance between that of air and/or water and that of the piezoelectric layer. In addition, as one skilled in the art will appreciate, an epoxy or polymer can be mixed with metal and/or ceramic powder of various compositions and ratios to create a material of variable acoustic impedance and attenuation. Any such combinations of materials are contemplated in this disclosure. The choice of matching layer(s), ranging from 1-6 discrete layers to one gradually changing layer, and backing layer(s), ranging from 0-5 discrete layers to one gradually changing layer alters the thickness of the piezoelectric layer for a specific center frequency.

In one aspect, the backing layer of the transducer can be configured such that the acoustic energy that travels downwards towards the backing layer when the piezoelectric element is electrically excited, or operated in receive mode, is absorbed by the backing material to avoid any unnecessary acoustic reflections within the thickness of the ultrasonic transducer stack. In one aspect, to effect the desired absorption of the acoustic energy that enters the backing material, a single backing material that has a high acoustic attenuation is configured to be sufficiently thick such that the layer acts as an infinitely thick layer. If more than a single backing layer is contemplated, to adjust the bandwidth and/or the characteristic frequency response of the transducer in any way, then the acoustic impedances are to be chosen accordingly. In one exemplary aspect, the backing layer can comprise a powder-doped epoxy.

In one aspect, a lens can be positioned in substantial overlying registration with the top surface of the layer that is the uppermost layer of the stack. The lens can be used for focusing the acoustic energy. The lens can be made of a polymeric material as would be known to one skilled in the art. In one preferred aspect, the lens can be made of a material that is well matched to water and has a low acoustic loss. For example, a preformed or prefabricated piece of Rexolite which has three flat sides and one curved face can be used as a lens. The radius of curvature (R) is determined by the intended focal length of the acoustic lens. For example not meant to be limiting, the lens can be conventionally shaped using computerized numerical control equipment, laser machining, molding, and the like. In one aspect, the radius of curvature is large enough such that the width of the curvature (WC) is at least as wide as the opening defined by the dielectric layer. Exemplary lens materials are polymethylpentene (e.g., TPX®) and cross-linked polystyrene (e.g., Rexolite®).

The speed of sound of Rexolite is greater than the speed of sound in water; therefore, the lens is formed with a concave surface. The radius of curvature of the lens defines the elevation focal depth of the array. For a focal length of 10 mm, the radius of curvature (R)=3.65 mm. In a further aspect, the maximum depth of the curvature of the lens can be minimized to avoid trapping air pockets in the acoustic gel used during imaging. In an additional aspect, the thinnest cross-sectional portion of the lens can be made as thin as possible such that the internal acoustic reflection that forms at the front face of the lens will remain temporally close to the primary pulse. In a further aspect, the thinnest cross-sectional portion of the lens can be thick enough to pass IEC patient leakage current tests for BF and/or CF rating. In yet another aspect, the curvature of the lens can extend beyond the active area of the array in order to avoid any unwanted diffraction due to a lens boundary discontinuity. Exemplary focal depths and radius of curvature of an exemplary Rexolite lens are:

| Approx Frequency Range | Lens Focal Depth | Rexolite Radius of Curvature |
| --- | --- | --- |
| 13-24 MHz | 15 mm | 5.45 mm |
| 18-42 MHz | 10 mm | 3.65 mm |
| 18-42 MHz | 9 mm | 3.30 mm |
| 22-55 MHz | 7 mm | 2.55 mm |
| 22-55 MHz | 6 mm | 2.20 mm |
| 30-70 MHz | 5 mm | 1.85 mm |

In one preferred aspect, the minimum thickness of the lens substantially overlies the center of the opening or gap defined by the dielectric layer. Further, the width of the curvature is greater than the opening or gap defined by the dielectric layer. In one aspect, the length of the lens can be wider than the length of a kerf slot allowing for all of the kerf slots to be protected and sealed once the lens is mounted on the top of the transducer device.

At least one first kerf slot can extend through or into at least one layer to reach its predetermined depth/depth profile in the stack. Some or all of the layers of the stack can be cut through or into substantially simultaneously. Thus, a plurality of the layers can be selectively cut through substantially at the same time. Moreover, several layers can be selectively cut through at one time, and other layers can be selectively cut through at subsequent times, as would be clear to one skilled in the art. In one aspect, at least a portion of at least one first and/or second kerf slot extends to a predetermined depth that is at least 60% of the distance from the top surface of the piezoelectric layer to the bottom surface of the piezoelectric layer, and at least a portion of at least one first and/or second kerf slot can extend to a predetermined depth that is 100% of the distance from the top surface of the piezoelectric layer to the bottom surface of the piezoelectric layer.

At least a portion of at least one first kerf slot can extend to a predetermined depth into the dielectric layer and at least a portion of one first kerf slot can also extend to a predetermined depth into the backing layer. As would be clear to one skilled in the art, the predetermined depth into the backing layer can vary from 0 microns to a depth that is equal to or greater than the thickness of the piezoelectric layer itself. Laser micromachining through the backing layer can provide a significant improvement in isolation between adjacent elements. In one aspect, at least a portion of one first kerf slot extends through at least one layer and extends to a predetermined depth into the backing layer. As described herein, the predetermined depth into the backing layer may vary. The predetermined depth of at least a portion of at least one first kerf slot can vary in comparison to the predetermined depth of another portion of that same respective kerf slot or to a predetermined depth of at least a portion of another kerf slot in a lengthwise direction substantially parallel to the longitudinal axis of the stack. In another aspect, the predetermined depth of at least one first kerf slot can be deeper than the predetermined depth of at least one other kerf slot.

As described above, at least one second kerf slot can extend through at least one layer to reach its predetermined depth in the stack as described above for the first kerf slots. The second kerf slots can extend into or through at least one layer of the stack as described above for the first kerf slots. If layers of the stack are cut independently, each kerf slot in a given layer of the stack, whether a first or second kerf slot can be in substantial overlying registration with its corresponding slot in an adjacent layer.

A transducer may also include a support member to provide mechanical support for the various components of the transducers and to aid in the fabrication process.

The invention will now be described with respect to the transducer configurations shown generally in FIGS. 1-23. An ultrasonic transducer includes a stack 800 having a first face 802, an opposed second face 804, and a longitudinal axis Ls extending between. The stack has a plurality of layers, each layer having a top surface 828 and an opposed bottom surface 830. The plurality of layers of the stack includes, for example, a piezoelectric layer 806, a dielectric layer 808, and a plurality of matching layers. The dielectric layer may be connected to and underlie at least a portion of the piezoelectric layer. In one example, the plurality of matching layers includes four matching layers in the stack.

The plurality of layers of the stack can further include a ground electrode layer 810 that is disposed on the top surface of the piezoelectric layer, a signal electrode layer 812, and a backing layer 814.

Figure 3:
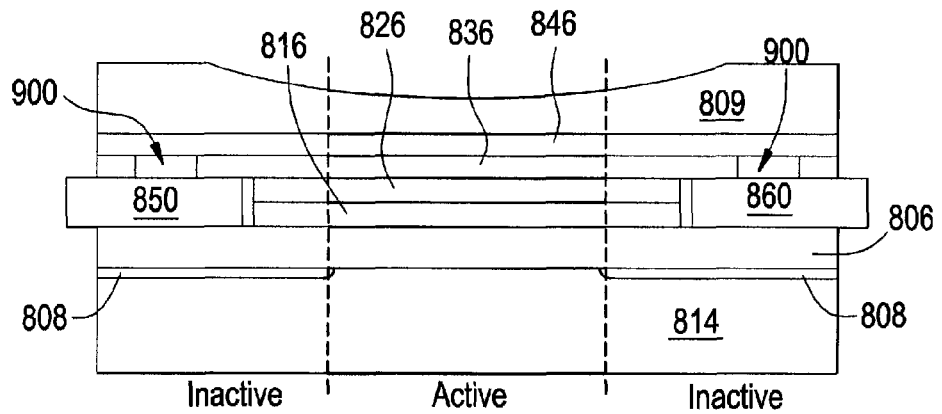
FIG. 3 is an exemplary cross-sectional view of the PZT stack of FIG. 1 showing the active and inactive areas of the transducer.
Figure 4:
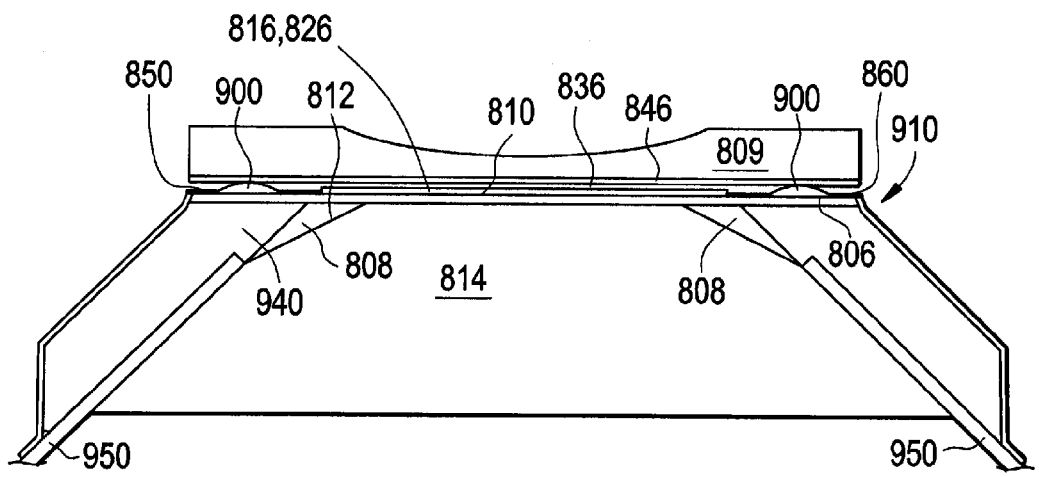
FIG. 4 is a cross-sectional view of the completed PZT stack shown mounted to a support member and showing the backing layer and dielectric layer. The signal electrodes (which are not shown herein but overlay portions of the dielectric layer between the array elements and the respective flex circuits) operatively couple the flex circuits to particular array elements defined therein the PZT stack and the ground electrodes are electrically coupled to the ground of the respective flex circuits.
Figure 5:
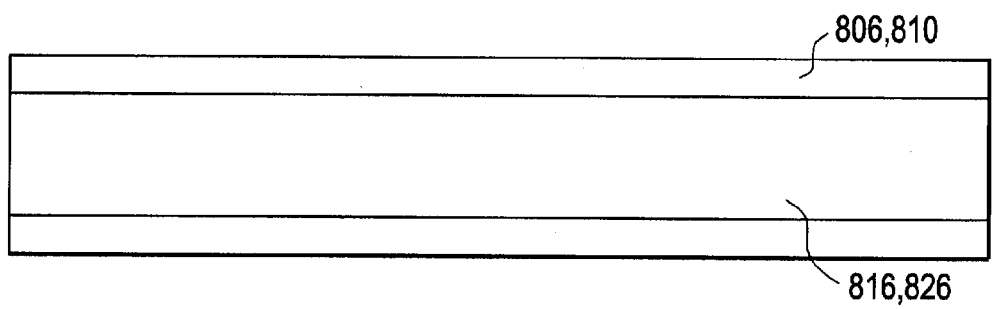
FIG. 5 is a top plan view of the top of the PZT stack with matching layers 1 and 2 shown attached.

As shown in FIGS. 1 and 3, the transducer stack defines an active area and an inactive area, in which a dielectric layer is provided under the ground electrode that acts as a potential divider and limits the voltage applied across the piezoelectric layer. In the figure, the stack includes the following layers in the active area (from top to bottom):

| Layer | Material | Zac (MRayl) | 20 MHz (μm) | 30 MHz (μm) | 30 MHz (μm) | 40 MHz (μm) | 50 MHz (μm) |
|---|---|---|---|---|---|---|---|
| Lens | Rexolite | 2.47 | 250 mm (Minimum thickness) | | | | |
| 4th Matching Layer | CA | 2.69 | 26.9 um | 17.9 um | 17.9 um | 13.4 um | 10.8 um |
| 3rd Matching Layer | SiC Epoxy | 3.45 | 33.1 um | 22.1 um | 22.1 um | 16.6 um | 13.3 um |
| 2nd Matching Layer | W/SiC Epoxy | 5.50 | 26.3 um | 17.5 um | 17.5 um | 13.1 um | 10.5 um |
| 1st Matching Layer | W Epoxy | 11.05 | 21.3 um | 14.2 um | 14.2 um | 10.6 um | 8.5 um |
| Ground Electrode | Au | 62.60 | Thin Layer ~8000 Å | | | | |
| Piezoelectric | PZT | 33 | 75 um | 51 um | 45 um | 39 um | 25 um |
| Signal Electrode | Au | 62.60 | ~10000 Å | | | | |
| Backing | PZT Epoxy | 8.50 | >5 mm | | | | |

In the inactive area, the stack transducer includes the following layers (from top to bottom):

| Layer | Material | Zac (MRayl) | 20 MHz Thicknesses | 30 MHz Thicknesses | 30 MHz Thicknesses | 40 MHz Thickness | 50 MHz Thickness |
|---|---|---|---|---|---|---|---|
| Lens | Rexolite | 2.47 | | | <0.5 mm | | |
| 4th Matching Layer | CA | 2.69 | 26.9 um | 17.9 um | 17.9 um | 13.4 um | 10.8 um |
| Copper Foil | Copper | N/A | 20 um | 20 um | 20 um | 20 um | 20 um |
| 3rd Matching Layer | SiC Epoxy | 3.45 | As required for active area thickness to be achieved | As required for active area thickness to be achieved | As required for active area thickness to be achieved | As required for active area thickness to be achieved | As required for active area thickness to be achieved |
| 2nd Matching Layer | W/SiC Epoxy | 5.50 | 26.3 um | 17.5 um | 17.5 um | 13.1 um | 10.5 um |
| 1st Matching Layer | W Epoxy | 11.05 | 21.3 um | 14.2 um | 14.2 um | 10.6 um | 8.5 um |
| Ground Electrode | Au | 62.60 | Thin Layer ~8000 Å | | | | |
| | Copper | N/A | Foil ~15-25 um thick | | | | |
| Dielectric | Silica Epoxy | N/A | >20 um | | | | |
| Piezoelectric | PZT | 33 | 75 um | 51 um | 45 um | 39 um | 25 um |
| Signal Electrode | Au | 62.60 | ~10000 Å | | | | |
| Backing | PZT Epoxy | 8.50 | >5 mm | | | | |

The piezoelectric layer 806 can be made of a variety of materials. For example and not meant to be limiting, materials that form the piezoelectric layer can include ceramic, single crystal, polymer and co-polymer materials, ceramic-polymer and ceramic-ceramic composites with 0-3, 2-2 and/or 3-1 connectivity, and the like. In one example, the piezoelectric layer includes lead zirconate titanate (PZT) ceramic.

Figure 6:
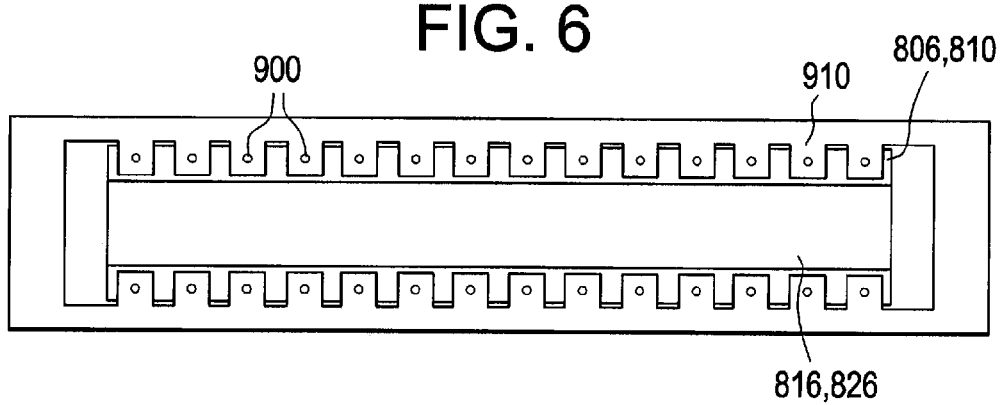
FIG. 6 is a top plan view of the top of the PZT stack with a copper foil mounted thereto with a conductive adhesive. Although the exemplified foil extends beyond the azimuth length of the PZT stack, these two end flaps are eventually removed in a subsequent fabrication step.
Figure 7:
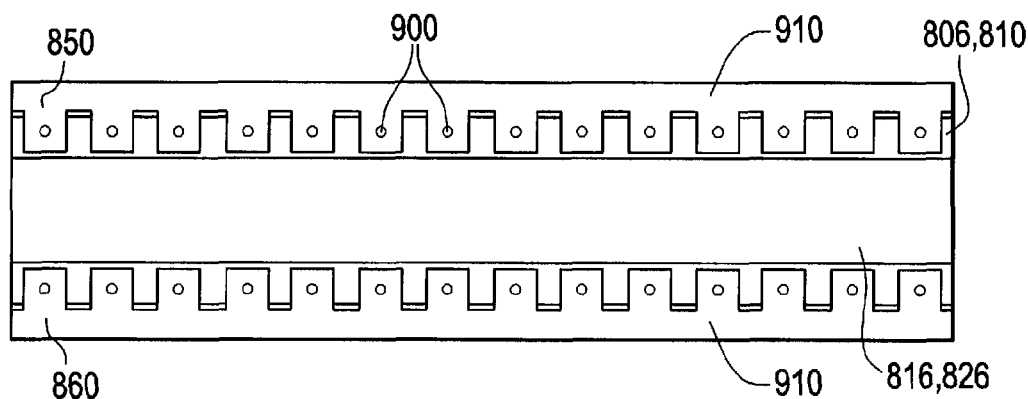
FIG. 7 is a plan view of top of the PZT stack of FIG. 6, with the end flaps of the copper foil removed.

As shown in FIGS. 6-7, the inner edges of the respective first and second ground electrodes can have a saw-tooth or stepped design that aids in avoiding any fault lines when the ground electrode is bonded to the piezoelectric layer. In a further aspect, the outer edges of the respective first and second ground electrodes are configured to extend beyond the respective longitudinal face edges of the piezoelectric layer so that they can be positioned as desired in electrical communication with a circuit board to form the desired ground connection. Thus, in one aspect, part of the ground electrode layer typically remains exposed in order to allow for the signal ground to be connected from the ground electrode to the circuit board.

In a further aspect, the inner edges of the respective first and second ground electrodes are spaced from each other a distance sufficient for respective first and second matching layers to be mounted sequentially on the top surface of the piezoelectric layer between the inner edges of the respective first and second ground electrodes. In this aspect, the longitudinally extending edges of the first and second matching layers 816, 826 can be spaced from the inner edges of the respective first and second ground electrodes 850, 860, respectively. Optionally, a plurality of spacers 900 can be provided that are positioned outside of the acoustic field as defined by the active area of the stack onto portions of the top surface of the respective first and second ground electrodes. Each spacer 900 extends upwardly a predetermined distance relative to the top surface of the piezoelectric layer such that the bottom surface of a fourth matching layer 846 can be positioned at a desired distance relative to the piezoelectric layer and the intervening first and second matching layers. In this aspect, one spacer can be positioned or formed on the inwardly extending portion of the saw-tooth inner edges of the respective first and second ground electrodes. In one aspect, upon completion of the assembly of the stack, the spacing generated by the spacers 900 is equal to the thickness of a third matching layer 836 of the stack. It is contemplated that the spacers can be made from any material that can be lapped down to, or built up to, the target thickness.

In one exemplary aspect, the dielectric material includes silica doped Epotek 301 epoxy, which has a low relative dielectric constant of about 4 and provides strong adhesion for sputtered gold when the dielectric surface is treated with low fluence UV light and/or plasma. In a further aspect, the thickness of the dielectric can be at least 10 μm, preferably at least 10 µm, and more preferably at least 20 µm. Optionally, the edge of the dielectric layer can be sloped, with respect to the cross-sectional plane, to provide some apodization and to help suppress side lobes in elevation. The exact shape of the slope will be selected by one skilled in art based on the desired effect on the ultrasound wave. In another aspect, the width of the gap in the doped epoxy dielectric layer, which defines the elevation dimension of the array, can preferably be between about 0.5 mm-3.5 mm, more preferably between about 0.75 mm-3.0 mm, and most particularly between about 1.0 mm-3.0 mm.

The plurality of layers of the stack can further include at least one matching layer having a top surface and an opposed bottom surface. In a further aspect, the acoustic impedance of each matching layer can be configured such that the acoustic impedance monotonically decreases from the first matching layer above the piezoelectric to the top matching layer just underneath the lens. In one exemplary aspect, at least one of the matching layers is polymer based. It is also contemplated that all of the matching layers can be polymer based. In a further aspect, the exemplary plurality of matching layers can result in a substantially smooth pulse response with no perceivable phase discontinuities. The smooth nature of the pulse response means that there is a predictable relationship between the time and frequency response of the transducer.

In one exemplary illustrated aspect, the plurality of matching layers comprises four such matching layers. In one exemplary aspect, at least a portion of the bottom surface of the first matching layer 816 can be connected to at least a portion of the top surface of the ground electrode layer, which is, as described above, mounted thereon the top surface of the piezoelectric layer. At least a portion of the bottom surface of the second matching layer 826 is connected to at least a portion of the top surface of the first matching layer. The first and second matching layers can be at least as long as the second predetermined length of the opening defined by the dielectric layer in a lengthwise direction substantially parallel to the longitudinal axis of the stack.

Figure 8:
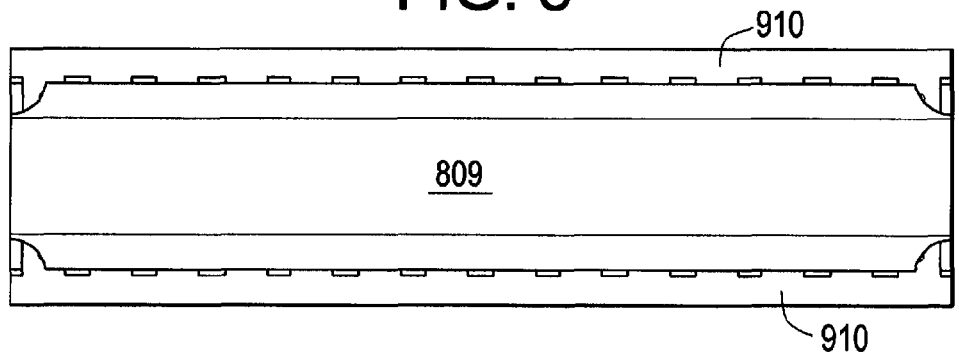
FIG. 8 is a top plan view of the top of the PZT stack with lens mounted thereto.
Figure 9:
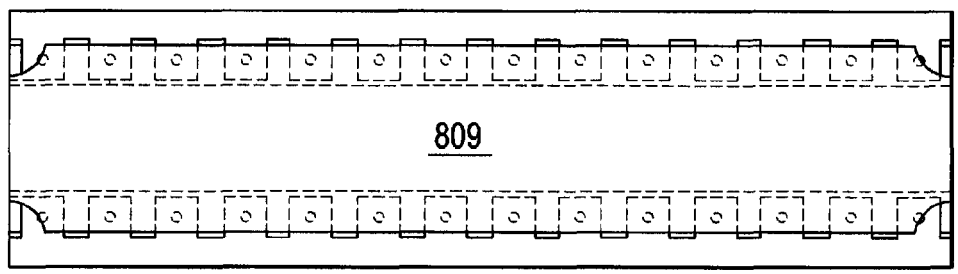
FIG. 9 is a top plan view of the top of the PZT stack showing the lens as a transparent layer in order to appreciate the alignment of the underlying layers as well as the relative alignment and positioning of the copper foil, the spacers, and the radius of curvature of the lens.

As shown in FIGS. 8-9, a lens 809 can be positioned in substantial overlying registration with the top surface of the matching layer that is the uppermost layer of the stack. In this aspect, the lens is a fixed lens that can be used for focusing the acoustic energy. For example, a preformed or prefabricated piece of Rexolite, which can have three flat sides and one curved face can be used as a lens. In a further aspect, the fixed lens 809 provides a means for focusing in elevation. The thickness of the lens can be thicker than the piezoelectric or matching layers.

In one aspect, a top surface of a fourth matching layer 846 is bonded to the bottom, flat face of the lens. In the embodiment in which the lens is formed from Rexolite, the fourth matching layer 846 can be made from cyanoacrylate (CA) adhesive, which is a low acoustic material that can be reliably bonded to the Rexolite lens, as described in U.S. Publication No. 2007/0205698. Of course, it is contemplated that any low impedance material that can be reliably bonded to the material of the desired lens can be used. In one further aspect, it is preferred that the bottom surface of the CA layer, i.e., the fourth matching layer, is adhesively coupled to the top surface of the second matching layer. In this aspect, of the bottom surface of the fourth matching layer are seated on the top surface of the plurality of spacers such that the lens can be positioned/spaced as the desired distance from the second matching layer. In this aspect, the adhesive layer provides for bonding the lens to the stack.

The applied adhesive layer can also act as the third matching layer 836 provided that the thickness of the adhesive layer applied to the bottom face of the lens is of an appropriate wavelength in thickness (such as, for example and not meant to be limiting, ¼ wavelength in thickness). In this example, it is contemplated that the choice of powder and concentration of powder is selected to adjust the acoustic impedance to match the desired acoustic profile. One skilled in the art will appreciate that Epotek 301 epoxy, Epotek 301-2 epoxy, and the like can be used as the adhesive layer to form the noted third matching layer. Epotek 301 epoxy has an acoustic impedance of 2.9 Mrayl in its pure state and can be doped with powders of different composition and size to create a 0-3 composite material that can be configured to have a desirable acoustic impedance by controlling the density and speed of sound. In this exemplary aspect, the layer of CA acts as one of the matching layers of the transducer. Thus, in one non-limiting example, the plurality of matching layers can comprise a layer of CA and three underlying matching layers can comprise powder loaded Epotek 301 epoxy, Epotek 301-2 epoxy, and the like.

In a further aspect, prior to mounting the lens onto the stack, the CA layer and the lens can be laser cut, which effectively extends the array kerfs (i.e., the first and/or second array kerf slots), and in one aspect, the sub-diced or second kerfs, through both matching layers (or if two matching layers are used) and into the lens. If the CA and lens are laser cut, a pick and place machine (or an alignment jig that is sized and shaped to the particular size and shape of the actual components being bonded together) can be used to align the lens in both X and Y on the uppermost surface of the top layer of the stack. To laser cut the CA and lens, laser fluence of approximately 0.5-5 J/cm$^2$ can be used.

In various exemplary aspects, arrays have the following acoustic design characteristics:

|  | Center Frequency | | | | | |
| --- | --- | --- | --- | --- | --- | --- |
|  | 20 MHz | 30 MHz | 30 MHz | 40 MHz | 40 MHz | 50 MHz |
| Elements | 256 | 256 | 256 | 256 | 256 | 256 |
| Pitch | 90 um (1.2 lambda) | 75 um (1.5 lambda) | 60 um (1.2 lambda) | 55 um (1.4 lambda) | 55 um (1.4 lambda) | 38 um (1.2 lambda) |
| Elevation | 2.8 mm | 2.0 mm | 2.0 mm | 1.4 mm | 1.2 mm | 1.0 mm |
| Focal Depth | 15 mm | 10 mm | 9 mm | 7 mm | 6 mm | 5 mm |
| Pulse Response | 60 ns (−6 dB) 120 ns (−20 dB) | 45 ns (−6 dB) 90 ns (−20 dB) | 45 ns (−6 dB) 85 ns (−20 dB) | 35 ns (−6 dB) 70 ns (−20 dB) | 35 ns (−6 dB) 70 ns (−20 dB) | 35 ns (−6 dB) 70 ns (−20 dB) |
| 2-Way Bandwidth | >65% (−6 dB) | >65% (−6 dB) | >65% (−6 dB) | >65% (−6 dB) | >65% (−6 dB) | >65% (−6 dB) |
| Directivity | >+/−15° | >+/−15° | >+/−15° | >+/−15° | >+/−15° | >+/−15° |

Example 1

Patterning of Electrodes

A flex circuit is placed on a 45 degree inclined plane with respect to the plane of an ultrasound array, and each finger of the flex is lined up with a corresponding array element. Two pieces of flex, one on each side of the array, are staggered, so that each flex is twice the pitch of the array. The flex is permanently attached in this position. The whole assembly is filled with a silica particle filled epoxy that covers all of the flex fingers. The epoxy is shaped to form a smooth internal profile over the all of the array, so that there are no sudden transitions from one surface to another.

An excimer laser is then used (e.g., 248 nm) to selectively expose the active region of the array by removing the particle/epoxy from the surface of the piezoelectric, e.g., PZT along each element, using a fluence that does not ablate the piezoelectric, but does remove the epoxy mixture. A ridge of kerf width is left between each element in the active area. The epoxy mixture is then removed from over the flex fingers, exposing the copper of the flex. Trenches are then made from each element to its respective finger. The transducer is sputtered, covering the entire inner surface with 1 µm of gold. Any standard metal could be used. A chromium adhesion layer may be used in conjunction with gold deposition. The laser ablation of the epoxy mixture and laser activation of the piezoelectric improve the adhesion of the metal.

A standard positive photoresist is coated onto the gold. Because of the trenches and ridges, the resist pools thickly in the trenches and remains thin on the high areas. The resist is allowed to dry but is not hard baked. The laser set to a very low fluence (about 0.3 J/cm$^2$) is used to remove the resist without damaging the gold underneath. This is important, since ablation of the gold directly will typically cause collateral damage to the electrode left behind. Having thus exposed the negative of the electrode pattern in the resist, the gold is etched using a standard wet gold etching process at slightly elevated temperatures of up to 50° C. for a few minutes. The result of this is to have removed almost all of the gold down to the Cr/Au alloy region that is only about 300 Angstroms thick.

The laser is used at a slightly higher fluence to remove the remaining metal, e.g., about 0.8 J/cm$^2$. This fluence will remove the remaining metal and created a trench in the epoxy under the gold layer. In the active area where the kerfs are less than 5 µm, a third, high fluence pass (e.g., at about 3 J/cm$^2$) may be used to remove shorts. The trench made with the 0.8 J/cm$^2$ pass acts as a guide for the plasma caused by the laser pulses, thereby preventing collateral damage of the electrode that would be caused by using a high fluence initially. After the final laser pass, a short wet etch can be used to de-burr the laser cut edges. Finally the resist is removed by dissolving in a suitable solvent at room temperature.

Example 2

Coupling a Transducer to Circuit

FIGS. 4-23 illustrate a methodology of preparing the transducer stack described above and operably coupling the transducer stack to a circuit board. Any of the embodiments described in the following may be employed generally with any method of the invention.

The piezoelectric layer, with a metalized ground electrode layer (not shown) coupled to the top surface of the piezoelectric layer, is initially blocked and its bottom surface is lapped conventionally to a first desired thickness in a first step. In one aspect, the first desired thickness is typically not the final thickness, but is rather a thickness that allows the continued working of the piezoelectric layer. In a second step, the first matching layer 816 is applied to a portion of the top surface of the metalized ground electrode layer and, after curing, is lapped to a target thickness. In step, the second matching layer 826 is applied to a portion of the top surface of the first matching layer and is subsequently lapped to a target thickness after curing. In one aspect, both the first and second matching layers are positioned substantially in the center of the piezoelectric layer and extend on the top surface of the piezoelectric layer between the elongate edges of the piezoelectric layer. The longitudinally extending edges of the first and second matching layers 816, 826 can be spaced from the longitudinally extending edges of the piezoelectric layer.

Subsequently, a copper foil 910 is coupled, for example with a conductive adhesive, to a portion of the top surface of the metalized ground electrode layer. As shown in FIG. 6, the copper foil is positioned to surround the first and second matching layers circumferentially. In a further aspect, the copper foil 910, which defines the respective first and second ground electrodes, is also positioned such that the inner edges of the respective first and second ground electrodes are spaced from the longitudinally extending edges of the respective first and second matching layers. Still further, the outward edges of the respective first and second ground electrodes extend outwardly beyond the longitudinal faces of the piezoelectric layer so that they can be operatively coupled to the ground of the circuit board in a latter step of the fabrication process. In a further aspect, as noted in the figure, the inner edges of the first and second ground electrodes can have a saw-tooth pattern that extends beyond the longitudinal faces of the piezoelectric layer so that the respective first and second ground electrodes can be readily bent along the respective longitudinal faces of the piezoelectric layer. As shown in FIG. 7, the respective ends of the copper foil are subsequently removed to physically separate the respective first and second ground electrodes. In one aspect, a contiguous copper foil is useful for the bonding of the copper foil to the piezoelectric layer. Optionally, the individual first and second ground electrodes could be mounted to the piezoelectric layer individually, which would result in the same structure as shown in FIG. 7. The first and second ground electrodes effectively act as extensions of the metalized ground electrode layer.

In another aspect, to achieve a desired standoff from the top surface of the respective first and second ground electrodes, a plurality of spacers 900 are positioned on portions of the top surface of the respective first and second ground electrodes. The plurality of spacers 900 can be in the form of pillars or dots that are positioned about the full perimeter of the piezoelectric layer. In another aspect, the plurality of spacers 900 can be positioned on portions of the top surface of the respective first and second ground electrodes adjacent to the inner edges of the respective first and second ground electrodes. In yet another aspect, the plurality of spacers can be positioned outwardly from the active area of the stack, i.e., in the inactive area of the stack. The spacers can be made from any conventional material that can be lapped to the desired target thickness.

The fourth matching layer 846 is adhesively coupled to the lens 809 and is subsequently allowed to cure prior to being lapped to the desired target thickness. In one exemplary aspect, the lens can include Rexolite, and the fourth matching layer can include a CA adhesive. In a further aspect, the fourth matching layer can be applied to a Rexolite blank and can be lapped to the desired target thickness prior to machining the Rexolite blank into a lens.

Referring to FIGS. 1 and 8-10], the fourth matching layer 846 is positioned on the top surfaces of the plurality of spacers to ensure that the adhesive that is used to bond the lens/fourth matching layer will form the third matching layer 836, which can have a desired target thickness as the adhesive cures. In another aspect, the bonded lens/fourth matching layer can be positioned in the substantial center of the stack in desired registration with the piezoelectric layer.

Referring now to FIGS. 11A and 11B, in one aspect, the bottom surface of the piezoelectric layer can be lapped to a desired thickness prior to the formation of the first and second kerf slots 818, 822, respectively. The first and second kerf slots are formed to the desired depth in the stack. The first and second kerf slots are machined in the stack from the bottom side of the stack. In one aspect, the first and second kerf slots are laser machined into the stack using a laser fluence of about and between 3-10 $J/cm^2$ and preferably about 5 $J/cm^2$. This laser fluence is adequate to create the kerf aspect ratios that are desired in the piezoelectric layer of the stack.

Further, in one aspect, a pin marker fiducial can be scribed on the bottom surface of the piezoelectric layer by, for example and not meant to be limiting, laser machining. The pin marker fiducial can be, for example, at least one marking, such as a plurality of crosses. The pin marker, if used, can be used to correctly orient the stack with respect to the flex circuit in a subsequent downstream fabrication process. In a further aspect, the pin marker fiducial should extend into the bottom surface of the piezoelectric layer a depth that is sufficient for the pin marker fiducial to remain visible as the bottom surface of the piezoelectric layer is lapped to its final target thickness. It is preferred that the etch pattern of the pin marker fiducial extend substantially straight down such that the width of the pin marker fiducial does not change when the bottom surface of the piezoelectric lapped.

As shown in FIGS. 11A and 11B, in a further aspect, laser alignment markers 930 can be scribed on the bottom surface of the piezoelectric layer by, for example, laser machining. The laser alignment markers 930 can be at least two markings, such as two crosses, one at either end of the stack. The laser alignment markers 930, if used, can be used to assist in the alignment and/or registration of the stack in subsequent downstream fabrication processes. In a further aspect, the alignment markers should extend into the bottom surface of the piezoelectric layer a depth that is sufficient for the markers to remain visible as the bottom surface of the piezoelectric layer is lapped to its final target thickness. It is preferred that the etch pattern of the laser alignment markers extend substantially straight down such that the width of the laser registration marker does not change when the bottom surface of the piezoelectric is lapped.

Figure 10:
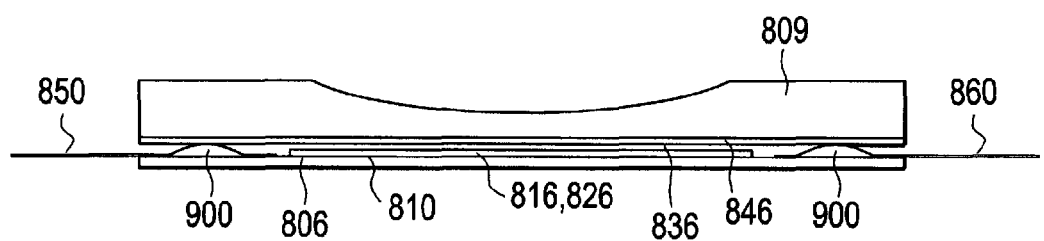
FIG. 10 is a schematic cross-sectional view of the PZT stack after the PZT has been lapped to final target thickness and is ready to be integrated with the flex circuit to create the array assembly. In this embodiment, the remaining layers of the stack are completed afterwards.

Optionally, the formed first and second kerf slots are filled as described above and the fill material is allowed to cure. Subsequently, the bottom surface of the piezoelectric layer is lapped to its final target thickness, which results in a cross sectional view of the stack that is illustrated in FIG. 10. One will appreciate that at this stage of the fabrication process, the dielectric layer, the signal electrode layer, and the backing layer have not been formed.

Figure 12A:
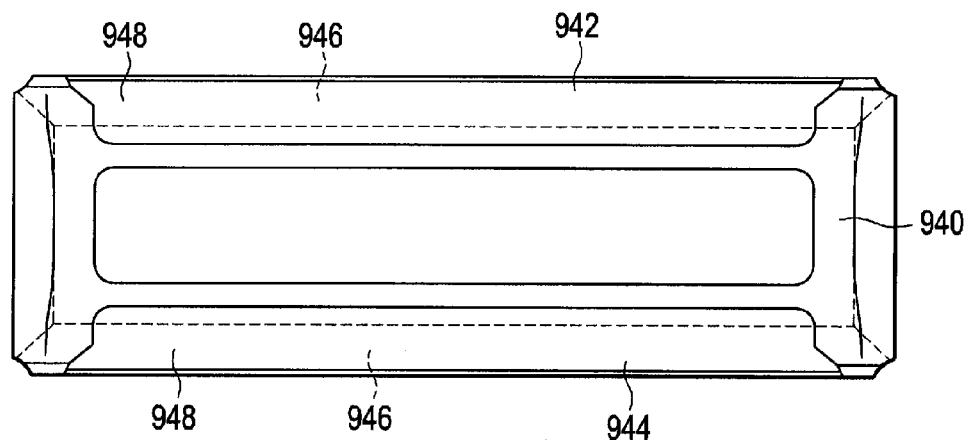
FIGS. 12A and 12B are a schematic top plan view and a perspective view of a support member for use with the PZT stack of FIG. 10, showing a first longitudinally extending side edge portion and an opposed second longitudinally extending side edge portion, each side edge portion having a respective inner surface and an opposed outer surface, wherein a portion of the respective inner surfaces of the first and second longitudinally extending side edge portions are configured so that a distal portion of a circuit board, such as, for example and without limitation, a flex circuit board, can be connected thereto, wherein the support member has a medial portion between the respective the first and second longitudinally extending side edge portions that defines a central, longitudinally extending opening, wherein the PZT stack of FIG. 10 is configured to mount on a portion of the medial portion of the support member.
Figure 12B:
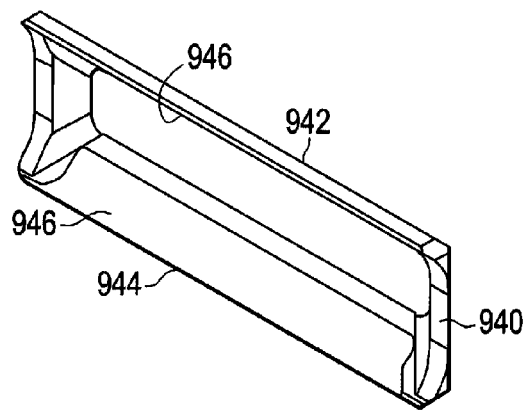
Figure 23:
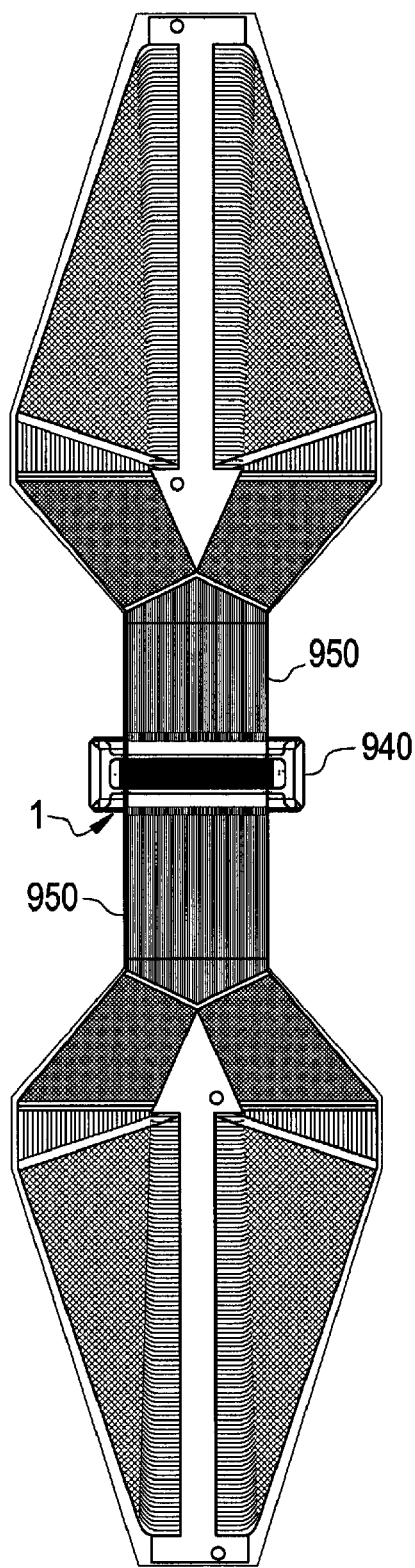
FIG. 23 is a schematic view showing a pair of flex circuits connected to an exemplary PZT stack. In one exemplary embodiment, pin 1 (i.e., element 1) of the assembly is indicated and is connected to the flex circuit on the left of the array assembly. In this non-limiting example, the flex circuit to the left of the array assembly is connected to the odd elements, and the flex circuit to the right of the array assembly is connected to the even elements.

Referring now to FIGS. 12A and 12B, an exemplary embodiment of a support member 940 is shown. The support member has a first longitudinally extending side edge portion 942 and an opposed second longitudinally extending side edge portion 944, each side edge portion having a respective inner surface 946 and an opposed outer surface 948, wherein a portion of the respective inner surfaces of the first and second longitudinally extending side edge portions are configured so that a distal portion of a circuit board, such as a flex circuit board, or circuit board pair, such as shown in FIG. 23, can be connected thereto. Other flex designs with fewer traces can be used. For example, more flex circuits would be required to sum up to a total of 256 traces. The support member also has a medial portion extending between the respective the first and second longitudinally extending side edge portions that define a central, longitudinally extending opening. The medial portion also provides mechanical strength and integrity to the support, necessary since the support, when bonded to the stack, will provide the mechanical support to prevent the stack from warping during the remainder of the assembly process. In one aspect, the first and second longitudinally extending side edge portions 942, 944 can be positioned at an acute angle relative to each other or, optionally, they can be positioned substantially parallel to each other or co-planar to each other.

In one exemplary aspect, a plurality of circuit alignment features 960, such as the exemplified score lines illustrated in FIGS. 14-15, are cut or otherwise conventionally formed into portions of the bottom surface of the medial portion of the support member. In this aspect, the plurality of circuit alignment features can be positioned such that they are adjacent to and/or extend to the respective first and second longitudinally extending side edge portions and/or the opening of the support member. One will appreciate that the plurality of circuit alignment features allows for the correct positioning of the distal portion of the lead frame (signal traces) of a circuit board, or circuit board pair, with respect to the first kerf slots cut within the stack. It is contemplated that the plurality of circuit alignment features on opposing sides of the opening of the support member are offset relative to each other by a distance equal to the pitch of the transducer array to allow for an alternating signal electrode pattern to be formed between the circuit board or circuit board pair and the array elements. In one aspect, the plurality of alignment features 960 can be formed in a separate step subsequent to mounting the stack to the support member. Optionally the plurality of alignment features can be formed prior to fixedly mounting the stack to the support member provided that the support can be mounted to the stack with adequate registration.

Figure 13:
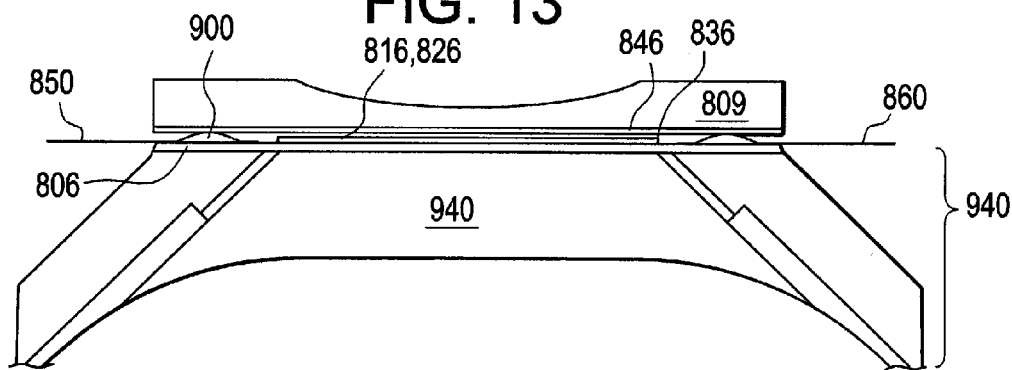
FIG. 13 is a schematic cross-sectional view of the support member of FIGS. 12A and 12B shown glued to the PZT stack of FIG. 10.

As shown in FIG. 13, the transducer stack is fixedly mounted thereto at least a portion of the top surface of the medial portion of the support member 940, and circuit alignment features are formed such that the circuit alignment features are positioned in registration with the array kerfs of the piezoelectric layer. In one aspect, the stack assembly can be adhesively bonded to the support member. It is contemplated that, in one aspect, the plurality of alignment features 960 can be formed in the support member in a separate step subsequent to fixedly mounting the stack to the support member. Optionally, the plurality of alignment features can be formed therein the support member prior to fixedly mounting the stack to the support member.

Figure 16:
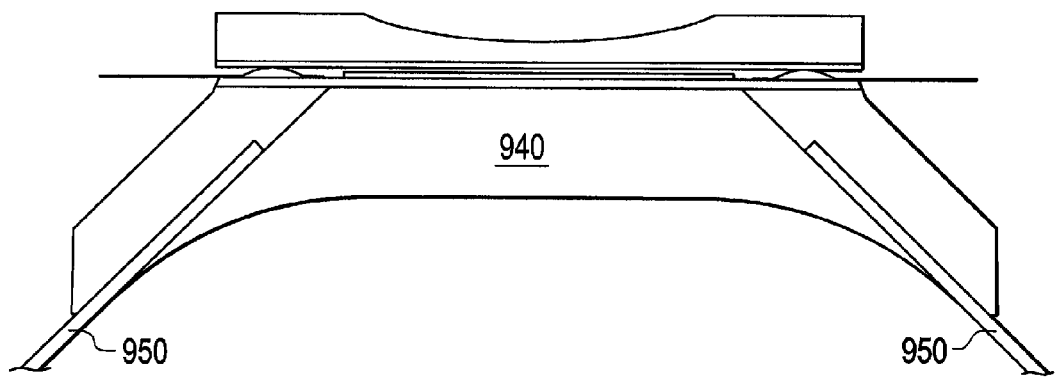
FIG. 16 is a schematic cross-sectional view of the PZT stack after it is die attached to the two flex circuits.

The respective bottom surface of the distal ends of the circuit boards, such as the flex circuit 950 shown in FIG. 16, are connected to the respective inner surfaces 946 of the first and second longitudinally extending side edge portions 942, 944. In one aspect, the flex circuit can be coupled to the support member by use of an adhesive, such as CA adhesive. The respective flex circuits are fixedly mounted to the respective inner surfaces of the first and second longitudinally extending side edge portions in registration with the plurality of circuit alignment features 960 to insure that the circuits on the respective circuit boards are aligned with the kerfs of the array transducer to within less than about a 0.5 pitch tolerance.

Figure 17:
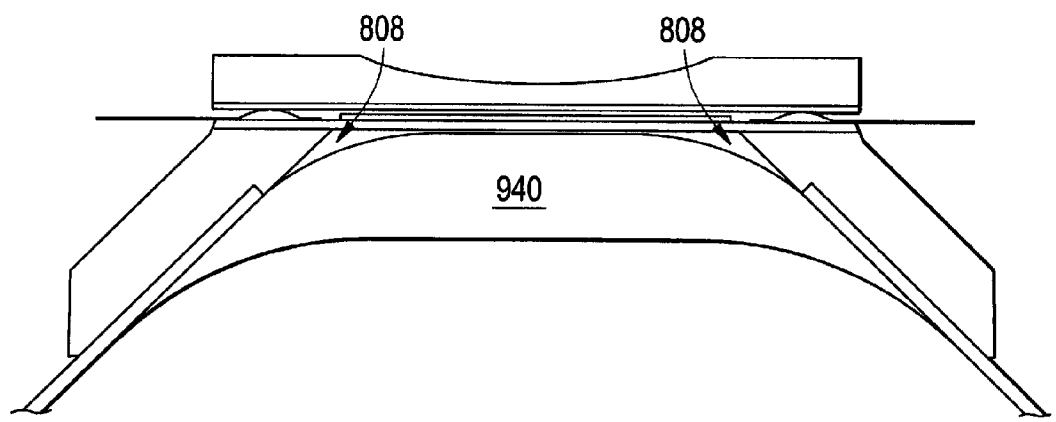
FIG. 17 is a schematic cross-sectional view showing an applied dielectric layer.

As shown in FIG. 17, a dielectric layer (e.g., a composite material as described herein) can be applied to the bottom portion of the array. In an optional step, the fiducial marking can be masked off prior to the application of the dielectric layer. In one aspect, the dielectric material can extend to cover the lead frame of the flex circuit, or flex circuit pair attached to the support frame. In one aspect, it is contemplated that the dielectric material could be applied separately from the dielectric material if so desired. In a further aspect, the profile of the dielectric layer is centered relative to the short axis of the piezoelectric stack, and it is configured such that the thickness of the dielectric layer that overlies the bottom surface of the piezoelectric layer meets the minimum electrical requirements to deactivate the piezoelectric. In another aspect, the dielectric layer can be configured such that the surface transition from the flex circuit to the bottom surface of the piezoelectric layer has a controlled cross-sectional profile that is void of sharp edges or undercuts in preparation for the deposition of the signal electrode layer. The transition of the dielectric from zero to target thickness allows for a relatively uniform thickness temporary conformal coating, such as, for example and not meant to be limiting, a resist material, to be applied on top of a blanket signal electrode layer, which allows for the use of a photoablation lithography process to be used during the subsequent patterning of the signal electrode layer.

Figure 18:
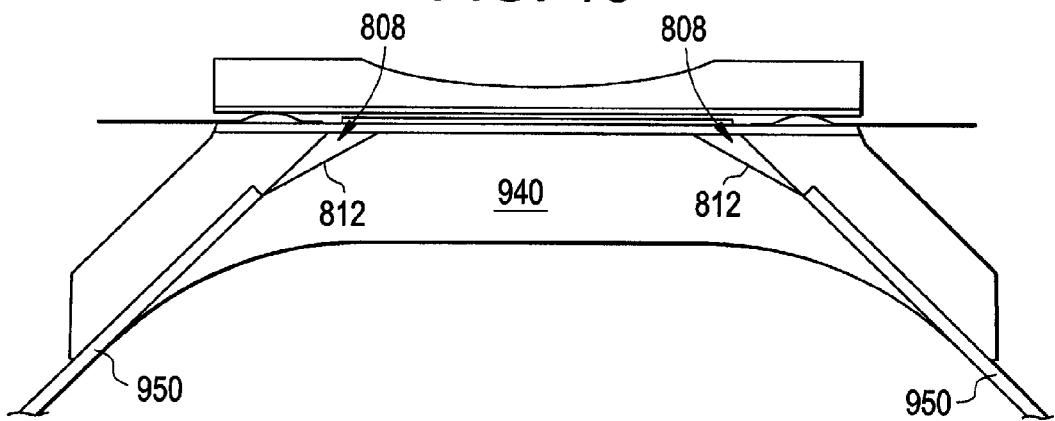
FIG. 18 is a schematic cross-sectional view of the finished dielectric layer. In this aspect, the dielectric layer defines the elevation dimension of the array and provides a smooth transitional surface from the flex to the stack in preparation for the deposition of the signal electrode.

In practice, it is preferred to apply the dielectric layer across the bottom portion of the piezoelectric stack as shown in FIG. 17 and subsequently to use a laser at a low fluence to trim away the dielectric in the active area and to create the smooth transition as shown in FIG. 18. Such a low fluence can safely and cleanly remove dielectric material without significantly ablating metal oxide powders, PZT, or the Cu metal on the flex circuit. In the non-limiting case of an Excimer laser, operating at 248 nm, a reasonable fluence is in the range of 0.5-1.5 $J/cm^2$. As described above, the formed opening in the dielectric layer defines the elevation of the array and the opening can have the following features: it can be narrower than the length of the first and second kerf slots relative to the short axis of the piezoelectric stack and/or it can be longer than the length of the plurality of first kerfs slots relative to the long axis of the piezoelectric.

Figure 19:
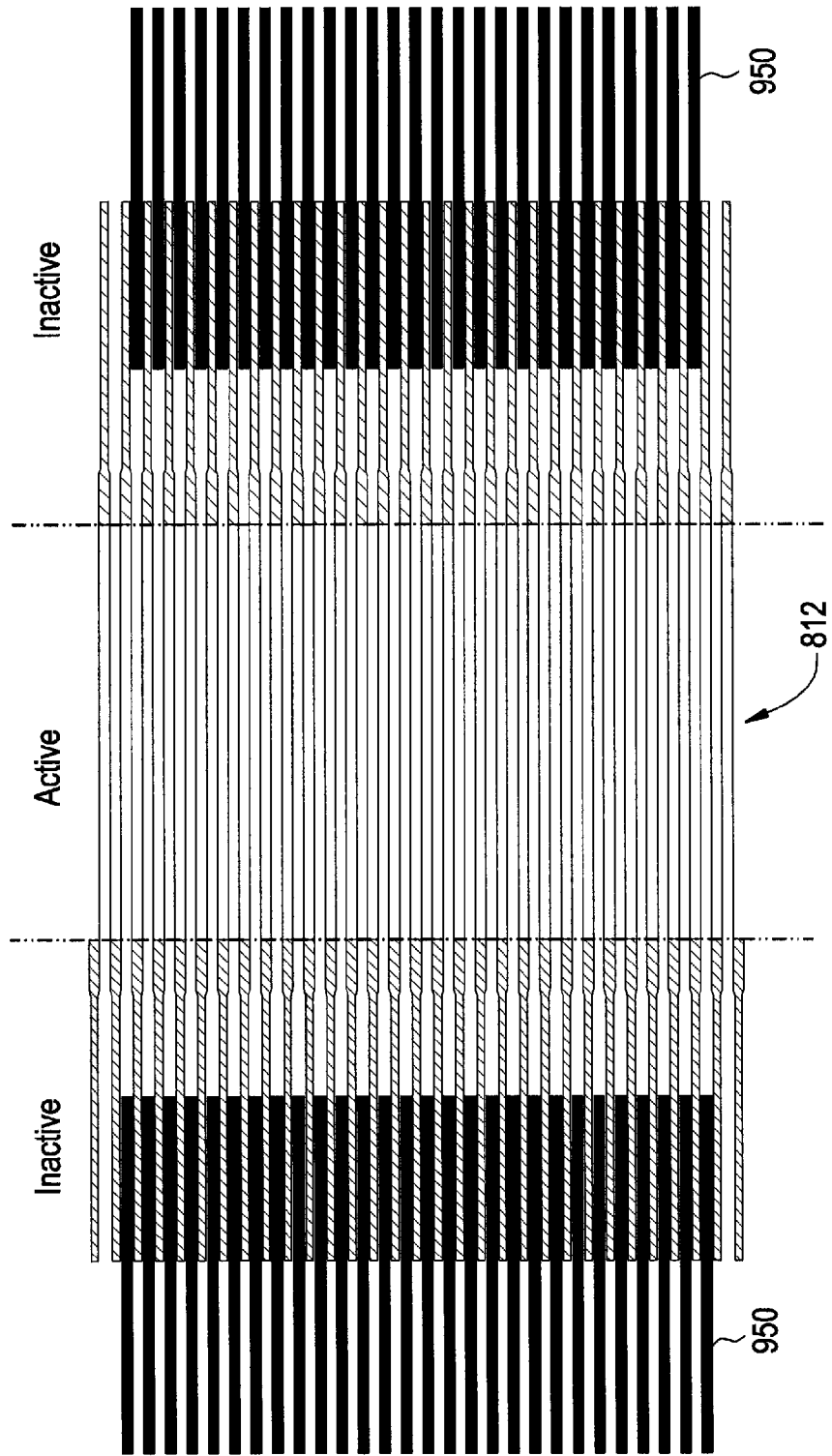
FIG. 19 is a schematic of the signal electrode pattern of the signal electrode layer. In this example, the hashed bars represent the removed electrode and the black bars represent the leadframe of each respective flex circuit. In this exemplary schematic, an additional electrode pattern above and below each flex circuit is shown. The dashed lines indicate the edge of the dielectric.

Referring to FIGS. 19 and 20, the patterning of the signal electrode layer and the electrical interconnect to the flex circuit, or flex circuit pair, can be accomplished using conventional packaging techniques such as, but not limited to photolithography and wirebonding, anisotropic conducting films and tapes, or direct contact between the stack and the flex leadframe. However, it is preferred that the patterning of the signal electrode layer be accomplished using a plurality of steps that can be scaled to frequencies higher than 50 MHz within a minimal packaging footprint volume. In one aspect, the signal electrodes are created by the following general steps (which are described in more detail below): surface preparation for electrode by means of laser photoablation; vacuum depositing a blanket signal electrode and shorting the bottom surface of the stack to all of the traces of the flex circuit, i.e., shorting a 256 array element of the stack to all 256 traces of the flex circuit; and combining laser photoablation lithography and chemical etching to pattern the isolated electrodes into the sputtered metal. In one aspect, it is contemplated that each signal electrode will be formed from gold (Au) and will be about and between 0.5-1.5 um thick; preferably about and between 0.6-1.2 um thick, and more preferably about and between 0.8-1.0 µm thick. The noted thickness for the gold electrodes allows the gold to behave like a macroscopic or bulk metal layer and have desired ductile and malleable properties, which increases the reliability of the device.

One will appreciate that a thin Cr, or Ti/W layer, of a few 100 Angstroms thick can be conventionally used as an adhesion layer, or that Nichrome is used as a diffusion barrier, when depositing a Au electrode. Conventionally, the thickness of these additional layers is very thin relative to the Au layer, and, in the case of alloying the metals by co-deposition, the amount of the alloy is not significant to impact the signal electrode patterning techniques described below. It is contemplated that all combinations of metal alloying is included when describing the patterning of the signal electrode.

Prior to depositing the signal electrode, a laser can be used to ensure that the desired portion of the bottom portion of the piezoelectric layer is fully exposed with no residual dielectric layer covering the piezoelectric in the active area. Further, the laser can pattern the dielectric layer that overlies the first kerf slots to form elevated ridges. One will appreciate that the formed ridges above the first kerfs slots, in the active area, will help reduce the thickness of the applied resist above the first kerf slots and allow the resist to pool above the piezoelectric. This aids in providing for clean kerf patterning of the signal electrode.

In another aspect, the laser can be used to form a shallow trench or sunken path that extends from each active element of the array to its designated copper trace on the flex circuit leadframe. The trenches in the dielectric from the active element to the flex circuit allow for resist to pool therein, which helps protect the Au during the patterning of the signal electrode. In yet another aspect, the laser can be used in this step to remove the dielectric material above the copper traces of the respective flex circuits and cleanly expose the copper traces.

Optionally, the laser can be used to create a "rough" textured surface on the portions of the array transducer that will be covered by the signal electrode. The textured surface can help to promote metal adhesion of the signal electrode to the surface, as described herein.

For an exemplary 256 element transducer array, the signal electrode layer forms a signal electrode pattern that is made of 256 isolated signal electrodes. In one aspect, each isolated signal electrode can have, in the active area of the stack, including the sloped transition to the dielectric layer, a minimum electrode gap, that is approximately as wide as the width of the first kerf slots between neighboring array elements. This electrode gap can extend from one side of the dielectric gap to the other and is preferably positioned substantially directly over the first kerf slots. Optionally, no electrode gap is required above the sub diced kerfs, i.e., the second kerf slots, because the sub diced piezoelectric bars are electrically shorted together as described above. In another aspect, on top of the dielectric layer, each isolated signal electrode can be terminated on the dielectric layer by removing the gold in between the two electrode gaps adjacent to each array element. As shown in FIGS. 19 and 20, the termination pattern alternates from left to right for each adjacent element and matches the flex circuit leadframe. In an additional aspect, an extension of the termination pattern from the stack onto the flex circuit can be provided on the top of the dielectric to complete the isolation of each signal electrode from adjacent elements. As one will appreciate, the extension of the termination pattern also alternates from left to right such that the extension falls in between two adjacent leads on the flex circuit.

In one embodiment, after the conventional deposition of an Au layer to the prepared portions of the transducer, a multistep laser ablation and etching process is used to create the intricate signal electrode pattern. In one exemplary aspect, the gold layer can be applied using conventional sputtering techniques. In a first step, a resist layer is applied to achieve a substantially even coat over the deposited gold layer. The stack may be tipped or rocked to help ensure that the resist coat is substantially even. In this aspect, it is contemplated that the resist will be allowed to dry at substantially room temperature. Elevated temperatures, below the soft baking temperature of the resist are also permitted provided that the temperature does not exceed the thermal budget or limits imposed by the materials and construct of the stack (for example and without limitation 50° C.). In a subsequent step, a laser, such as a laser using a low fluence of, for example, about 0.3 J/cm$^2$, can photoablate the resist over only the full signal electrode pattern, such as for example the full 256 array element signal electrode pattern. In a subsequent step, the signal electrode pattern is conventionally etched to thin the applied gold layer. Without limitation, this etching step can be exemplarily accomplished by warming the etching materials to 32° C. and etching for 3 minutes.

Subsequently, the laser can be applied substantially over the first kerf slots to help remove the majority of any residual metals that remain above the first kerf slots. Further, in this step, it is contemplated that a portion of the fill material therein the first kerf slot adjacent to the bottom surface of the piezoelectric layer will be removed. As one will appreciate, this removal of the fill material will create shallow trenches in the fill material within the first kerf slots that extend below the plane of the bottom surface of the piezoelectric layer. In one aspect, it is contemplated that the laser will use a medium fluence, i.e., about and between 0.3-0.8 J/cm$^2$, for this ablation step.

In a further aspect, it is contemplated that a general laser pass over the flex circuit and other potentially exposed areas at a low fluence level, i.e., about and between 0.3 and 0.4 J/cm$^2$, can be accomplished after each laser ablation step. This low fluence pass of the laser can help ensure that any residual, undesired post etched sputtered gold has been removed.

In an optional additional step, the laser can be additionally be applied at a high fluence for a minimal number of pulses over the first kerf slots and over the termination pattern to remove any burs that may have persisted at this stage of the signal electrode formation process. As one will appreciate, any sunken feature that had previously been formed can aid in protecting the deposited signal electrodes from the plasma plume created during the elevated fluence laser ablation process.

As one will appreciate, after the processing described above, each signal electrode is operatively mounted to the transducer and is electrically coupled to both an individual circuit of the flex circuit and an individual array element. Optionally, the signal electrodes are tested for shorts so that any short can be identified and targeted rework can be accomplished to rectify the identified shorts.

Optionally, an additional etching step can be performed to debur the signal electrode pattern. Without limitation, this etching step can be accomplished by warming the etching materials to 32° C. and etching for 1 minute. This step can aid in removing any final residuals that could risk causing shorts when the backing layer is applied. Finally, the resist is cleaned from the transducer/support member/flex circuit assembly, i.e., the array assembly, and the signal electrodes are again tested for shorts so that any short can be identified and targeted rework can be accomplished to rectify the identified shorts.

Figure 21:
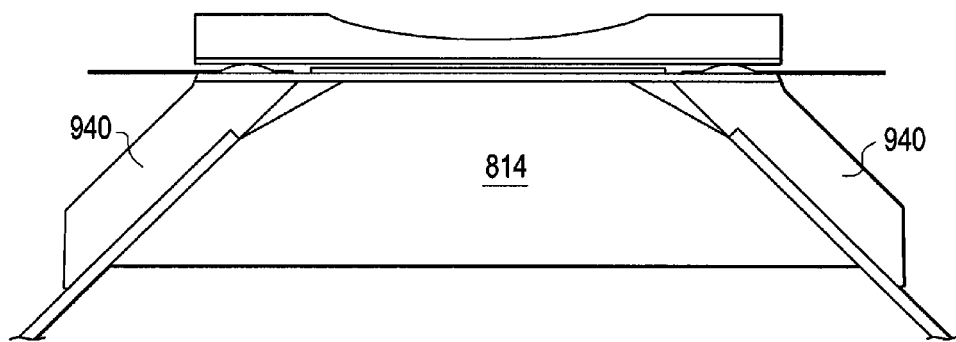
FIG. 21 is a schematic cross-sectional view illustrating the application of the backing material.

As shown in FIG. 21, the backing layer is applied to complete the array assembly. In one aspect, the backing layer can be positioned to cover and to extend beyond the active area of the stack. In a further aspect, the backing layer can substantially fill the cavity that is defined therein the support member between the respective inner surfaces of the first and second longitudinally extending side edge portions of the support member.

Figure 22A:
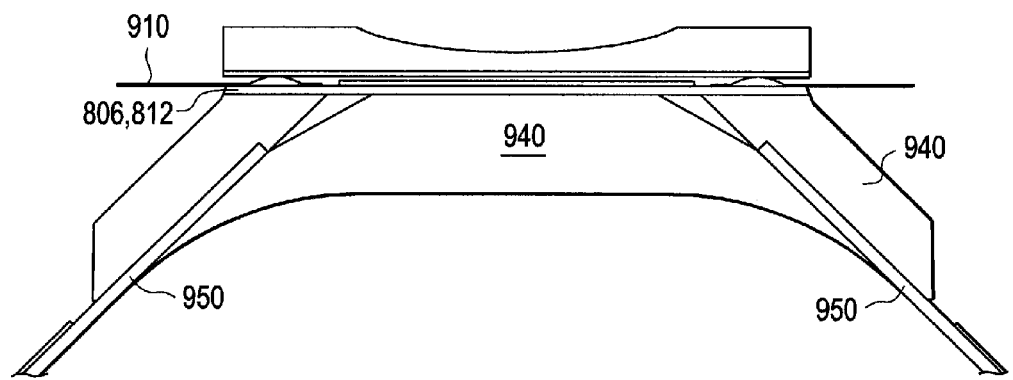
FIGS. 22A and 22B are schematic cross-sectional views of the array assembly mounted thereon the support member and prior to the deposition of the signal electrode pattern.
Figure 22B:
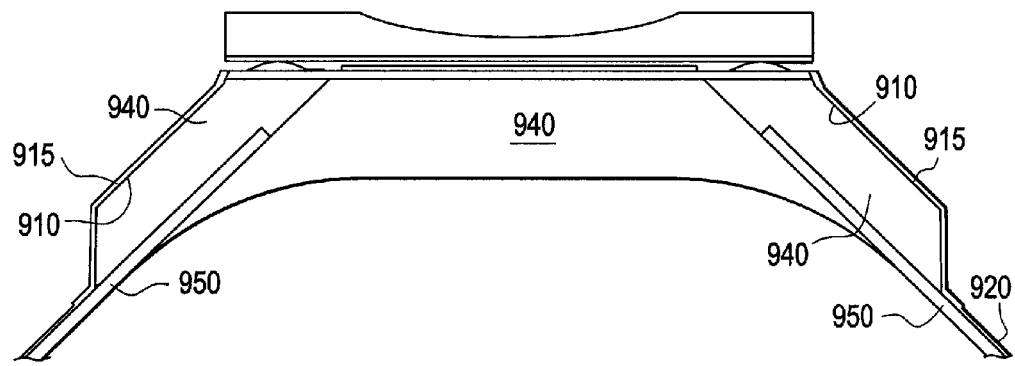

In an additional step and referring to FIGS. 22A and 22B, the signal return path from the stack to the coupled flex circuits should be operably coupled prior to the formation of the signal electrodes. This allows for the electrical integrity of the signal electrode to be tested after the signal electrode pattern has been created. In one aspect a conductive material, such as, copper tape 915 and the like, is positioned on the array assembly to electrically couple the respective first and second ground electrodes to the respective grounds 920 on the flex circuits. The copper tape can be bonded with additional conductive epoxy material or low temperature solder to form a reliable electrical contact. Thus, in one example, the signal return path from the assembly extends generally parallel to the kerfs to the end of the stack, up through the conductive epoxy bond line into the copper foil and then onto the flex circuit via the additional conductive path of the exemplary copper tape.

Other Embodiments

Throughout this application, various publications are referenced. The disclosures of these publications in their entireties are hereby incorporated by reference. Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Other embodiments are in the claims.

What is claimed is:

1. A method for producing electrodes in a pattern, comprising:
   (a) providing an ultrasound array transducer stack comprising a plurality of ultrasonic array elements;
   (b) placing a connector having an electrical connection for each of the plurality of ultrasonic array elements in proximity to the ultrasound array transducer stack;
   (c) depositing a composite dielectric material comprising a matrix material and a particulate material on the ultrasound array transducer stack and the connector, wherein the matrix material is laser ablatable at a lower fluence than the particulate material;
   (d) laser ablating the composite dielectric material to substantially expose the plurality of ultrasonic array elements and to form a plurality of trenches in the composite dielectric material, each of the plurality of trenches extending from one of the ultrasonic array elements to an electrical connection of the connector, wherein laser ablating the composite dielectric material includes removing matrix material and increasing a surface area of the composite dielectric material;

(e) depositing a conductive metal on the plurality of ultrasonic array elements and the plurality of trenches after laser ablating the composite dielectric material;

(f) depositing a resist on the conductive metal, such that the resist is thicker over each ultrasonic array element and each trench compared to areas between the ultrasonic array elements;

(g) removing a portion of the resist to expose a portion of the conductive metal in a pattern that is a negative of a desired pattern of electrodes; and (h) removing the exposed portion of the conductive.

2. The method of claim 1, wherein:
the ultrasound array transducer stack further comprises a plurality of first kerf slots that extend a predetermined depth therein the stack, and wherein the plurality of first kerf slots define the plurality of ultrasonic array elements;
the plurality of first kerf slots are not exposed by laser ablating the composite dielectric material;
the resist is thicker over each ultrasonic array element and each trench compared to the plurality of first kerf slots; and
the method further comprises (i) laser ablating the areas of etched conductive ultrasound array transducer stack to remove the composite dielectric material over the plurality of first kerf slots to create a depression between individual ultrasonic array elements.

3. The method of claim 2, further comprising (j) laser ablating the depressions between individual ultrasonic array elements, wherein step (j) occurs at a higher fluence than step (i).

4. The method of claim 3, further comprising removing the resist after step (j).

5. The method of claim 3, further comprising etching to remove conductive metal burrs produced by laser ablation in step (j).

6. The method of claim 2, wherein the plurality of first kerf slots are filled with a solid material, which is ablated in step (i).

7. The method of claim 2, wherein step (e) further comprises depositing an adhesion layer prior to the conductive metal.

8. The method of claim 7, wherein step (h) includes removing the conductive metal deposited on the adhesion layer.

9. The method of claim 8, wherein step (i) includes removing the adhesion layer exposed by step (h).

10. The method of claim 7, wherein the conductive metal is gold.

11. The method of claim 7, wherein the adhesion layer comprises chromium.

12. The method of claim 1, wherein no step occurs at higher than 70° C.

13. The method of claim 1, wherein step (g) comprises laser ablating the resist at a fluence insufficient to ablate the conductive metal.

14. The method of claim 1, wherein a pitch of the plurality of ultrasonic array elements is at most 100 µm.

15. The method of claim 1, wherein a pitch of the plurality of ultrasonic array elements is at most 65 µm.

16. The method of claim 1, wherein the matrix material comprises epoxy.

17. The method of claim 1, wherein the particulate material comprises silica, silicon carbide, or a combination thereof.

18. The method of claim 1, wherein laser ablating the composite dielectric material causes particles of the particulate material to be partially exposed and partially embedded in the matrix material.

19. A method, comprising:
depositing a composite dielectric material onto an electrical component including an array of ultrasound transducer elements, the composite dielectric material including a matrix material and a particulate material dispersed within the matrix material, the matrix material being laser ablatable at a lower fluence than the particulate material;
laser ablating the composite dielectric material to substantially expose each of the ultrasound transducer elements and to form a trench in the composite dielectric material extending from the ultrasound transducer element to another portion of the electrical component, wherein laser ablating the composite dielectric material includes removing matrix material and exposing particulate material to increase a surface area of the composite dielectric material;
depositing a conductive material on the ultrasound transducer element and the trench;
depositing a resist on the conductive material;
removing a portion of the resist to expose a portion of the conductive material; and
removing the exposed portion of the conductive material to form an electrode electrically connected to the ultrasound transducer element.

20. The method of claim 19, wherein laser ablating the composite dielectric material includes laser ablating the composite dielectric such that particles of the particulate material are partially exposed and partially embedded in the matrix material.

21. The method of claim 19, wherein the ultrasound transducer element is a first ultrasound transducer element, depositing the conductive material includes depositing the conductive material on an area between the first ultrasound transducer element of the ultrasound transducer elements, and depositing the resist on the conductive material includes depositing the resist on the conductive material such that the resist is thicker over the first ultrasound transducer element and the trench compared to the area between the first ultrasound transducer element and the second ultrasound transducer element.

22. The method of claim 19, wherein the electrical component includes a connector having an electrical connection for the ultrasound transducer element, and the electrode electrically connects the ultrasound transducer element to the electrical connection of the connector.

23. The method of claim 19, wherein removing a portion of the resist includes laser ablating the resist at a fluence insufficient to substantially ablate the conductive material.

24. The method of claim 19, wherein a pitch of the ultrasound transducer element is at most 100 µm.

25. The method of claim 19, wherein a pitch of the ultrasound transducer element is at most 65 µm.

26. The method of claim 19, wherein the matrix material includes epoxy.

27. The method of claim 19, wherein the particulate material includes silica, silicon carbide, or a combination thereof 28. The method of claim 19, wherein depositing the composite dielectric material, laser ablating the composite dielectric material, depositing the conductive material, depositing the resist, removing the portion of the resist, and removing the exposed portion of the conductive material occur at temperatures less than 70° C.

29. The method of claim 19, wherein laser ablating the composite dielectric material includes laser ablating the composite dielectric material to substantially expose a plurality of ultrasound transducer elements and to form a plurality of trenches in the composite dielectric material, each of the plurality of trenches extending from one of the plurality of ultrasound transducer elements to one of a plurality of other portions of the electrical component.

30. The method of claim 29, wherein depositing the conductive material includes depositing the conductive material on the plurality of ultrasound transducer elements and the plurality of trenches, and removing the exposed portion of the conductive material includes removing the exposed portion of the conductive material to form a plurality of electrodes, each of the plurality of electrodes being electrically connected to one of the plurality of ultrasound transducer elements.

31. The method of claim 19, further comprising depositing an adhesion layer prior to depositing the conductive material.

32. The method of claim 31, wherein the conductive material is gold.

33. The method of claim 31, wherein the adhesion layer includes chromium.

34. The method of claim 19, wherein the ultrasound transducer element is a first ultrasound transducer element, the electrical component includes a first kerf slot that extends a predetermined depth into the electrical component, the first kerf slot separates the first ultrasound transducer element from a second ultrasound transducer element in the array of ultrasound transducer elements, and the first kerf slot is not exposed by laser ablating the composite dielectric material.

35. The method of claim 34, further comprising depositing an adhesion layer prior to depositing the conductive material, and laser ablating the adhesion layer under the exposed portion of the conductive material after removing the exposed portion of the conductive material.

36. The method of claim 34, further comprising laser ablating the composite dielectric material over the first kerf slot to create a depression between the first ultrasound transducer element and the second ultrasound transducer element, wherein depositing the resist on the conductive material includes depositing the resist on the conductive material such that the resist is thicker over the first ultrasound transducer element and the trench compared to the first kerf slot.

37. The method of claim 36, further comprising laser ablating a solid material within the first kerf slot, wherein the solid material is a material other than the composite dielectric material.

38. The method of claim 36, wherein laser ablating the composite dielectric material over the first kerf slot includes laser ablating the composite dielectric material over the first kerf slot at a first fluence, and the method further comprises laser ablating the depression between the first ultrasound transducer element and the second ultrasound transducer element at a second fluence higher than the first fluence.

39. The method of claim 36, further comprising removing the resist after laser ablating the composite dielectric material over the first kerf slot.

40. The method of claim 36, further comprising etching the electrical component after laser ablating the composite dielectric material over the first kerf slot to remove conductive burrs.

* * * * *